United States Patent
Lynn et al.

(10) Patent No.: US 9,380,932 B1
(45) Date of Patent: Jul. 5, 2016

(54) RETRACTOR DEVICES FOR MINIMALLY INVASIVE ACCESS TO THE SPINE

(71) Applicant: Pinnacle Spine Group, LLC, Dallas, TX (US)

(72) Inventors: Jim R. Lynn, San Clemente, CA (US); Russell W. Nelson, Westlake Village, CA (US)

(73) Assignee: Pinnacle Spine Group, LLC, Dallas, TX (US)

( * ) Notice: Subject to any disclaimer, the term of this patent is extended or adjusted under 35 U.S.C. 154(b) by 122 days.

(21) Appl. No.: 13/666,829

(22) Filed: Nov. 1, 2012

Related U.S. Application Data

(60) Provisional application No. 61/554,958, filed on Nov. 2, 2011.

(51) Int. Cl.
*A61B 1/32* (2006.01)
*A61B 1/06* (2006.01)
*A61B 1/07* (2006.01)

(52) U.S. Cl.
CPC ................. *A61B 1/32* (2013.01); *A61B 1/0684* (2013.01); *A61B 1/07* (2013.01)

(58) Field of Classification Search
CPC ........................... A61B 17/70; A61B 17/0206
USPC .................................................. 600/201–246
See application file for complete search history.

(56) References Cited

U.S. PATENT DOCUMENTS

| | | | |
|---|---|---|---|
| 5,123,926 A | 6/1992 | Pisharodi | |
| 5,375,823 A | 12/1994 | Navas | |
| 5,489,307 A | 2/1996 | Kuslich et al. | |
| 5,593,409 A | 1/1997 | Michelson | |
| 5,609,635 A | 3/1997 | Michelson | |
| 5,653,763 A | 8/1997 | Errico et al. | |
| 5,665,122 A | 9/1997 | Kambin | |
| 5,669,909 A | 9/1997 | Zdeblick et al. | |

(Continued)

FOREIGN PATENT DOCUMENTS

| | | |
|---|---|---|
| EP | 425542 B1 | 3/1995 |
| EP | 793463 A1 | 9/1997 |

(Continued)

OTHER PUBLICATIONS

International Search Report for International Application No. PCT/US2011/028731 (a PCT counterpart of the present application) dated May 18, 2011.

(Continued)

*Primary Examiner* — Ellen C Hammond
*Assistant Examiner* — Christina NegrelliRodrigue
(74) *Attorney, Agent, or Firm* — Knobbe, Martens, Olson & Bear, LLP

(57) ABSTRACT

According to some embodiments, a retractor device for selectively moving (e.g., retracting) anatomical tissue of a subject during a minimally invasive procedure (e.g., accessing the lumbar or other portion of a spine during a spinal fusion procedure) comprises a main body comprising at least three sides (e.g., three, four, five sides, more than five sides, etc.). In some embodiments, the main body defines or otherwise forms a central opening, which comprises a center-point positioned along a centerline of the central opening. In some embodiments, the retractor device further comprises a plurality of movable members secured to the main body.

18 Claims, 19 Drawing Sheets

(56) References Cited

U.S. PATENT DOCUMENTS

| | | |
|---|---|---|
| 5,683,394 A | 11/1997 | Rinner |
| 5,702,455 A | 12/1997 | Saggar |
| 5,716,415 A | 2/1998 | Steffee |
| 5,749,916 A | 5/1998 | Richelsoph |
| 5,766,253 A | 6/1998 | Brosnahan, III |
| 5,772,661 A | 6/1998 | Michelson |
| 5,776,199 A | 7/1998 | Michelson |
| 5,782,919 A | 7/1998 | Zdeblick et al. |
| 5,860,973 A | 1/1999 | Michelson |
| 5,865,845 A | 2/1999 | Thalgott |
| 5,865,848 A | 2/1999 | Baker |
| 5,885,287 A | 3/1999 | Bagby |
| 5,888,223 A | 3/1999 | Bray, Jr. |
| 5,888,224 A | 3/1999 | Beckers et al. |
| 5,888,227 A | 3/1999 | Cottle |
| 5,895,427 A | 4/1999 | Kuslich et al. |
| 5,906,616 A | 5/1999 | Pavlov et al. |
| 5,910,315 A | 6/1999 | Stevenson et al. |
| 5,928,284 A | 7/1999 | Mehdizadeh |
| 5,947,971 A | 9/1999 | Kuslich et al. |
| 5,968,098 A | 10/1999 | Winslow |
| 5,976,187 A | 11/1999 | Richelsoph |
| 5,984,967 A | 11/1999 | Zdeblick et al. |
| 5,989,291 A | 11/1999 | Ralph et al. |
| 6,010,502 A | 1/2000 | Bagby |
| 6,019,792 A | 2/2000 | Cauthen |
| 6,033,438 A | 3/2000 | Bianchi et al. |
| 6,045,579 A | 4/2000 | Hochshuler et al. |
| 6,056,749 A | 5/2000 | Kuslich |
| 6,059,790 A | 5/2000 | Sand et al. |
| 6,074,423 A | 6/2000 | Lawson |
| 6,080,193 A | 6/2000 | Hochshuler et al. |
| 6,090,143 A | 7/2000 | Meriwether et al. |
| 6,096,080 A | 8/2000 | Nicholson et al. |
| 6,102,950 A | 8/2000 | Vaccaro |
| 6,106,557 A | 8/2000 | Robioneck et al. |
| 6,113,638 A | 9/2000 | Williams et al. |
| 6,117,174 A | 9/2000 | Nolan |
| 6,123,705 A | 9/2000 | Michelson |
| 6,126,689 A | 10/2000 | Brett |
| 6,129,763 A | 10/2000 | Chauvin et al. |
| 6,143,031 A | 11/2000 | Knothe et al. |
| 6,146,420 A | 11/2000 | McKay |
| RE37,005 E | 12/2000 | Michelson et al. |
| 6,159,244 A | 12/2000 | Suddaby |
| 6,159,245 A | 12/2000 | Meriwether et al. |
| 6,174,334 B1 | 1/2001 | Suddaby |
| 6,176,882 B1 | 1/2001 | Biedermann et al. |
| 6,190,414 B1 | 2/2001 | Young et al. |
| 6,193,756 B1 | 2/2001 | Studer et al. |
| 6,206,922 B1 | 3/2001 | Zdeblick et al. |
| 6,224,631 B1 | 5/2001 | Kohrs |
| 6,235,028 B1 | 5/2001 | Brumfield et al. |
| 6,241,733 B1 | 6/2001 | Nicholson et al. |
| 6,241,769 B1 | 6/2001 | Nicholson et al. |
| 6,241,770 B1 | 6/2001 | Michelson |
| 6,245,072 B1 | 6/2001 | Zdeblick et al. |
| 6,245,108 B1 | 6/2001 | Biscup |
| 6,258,094 B1 | 7/2001 | Nicholson et al. |
| 6,258,125 B1 | 7/2001 | Paul et al. |
| 6,283,968 B1 | 9/2001 | Mehdizadeh |
| 6,296,664 B1 | 10/2001 | Middleton |
| 6,306,170 B2 | 10/2001 | Ray |
| 6,332,894 B1 | 12/2001 | Stalcup et al. |
| 6,332,895 B1 | 12/2001 | Suddaby |
| 6,368,351 B1 | 4/2002 | Glenn et al. |
| 6,371,986 B1 | 4/2002 | Bagby |
| 6,371,987 B1 | 4/2002 | Weiland et al. |
| 6,371,988 B1 | 4/2002 | Pafford et al. |
| 6,371,989 B1 | 4/2002 | Chauvin |
| 6,375,655 B1 | 4/2002 | Zdeblick et al. |
| 6,395,035 B2 | 5/2002 | Bresina et al. |
| 6,409,766 B1 | 6/2002 | Brett |
| 6,419,705 B1 | 7/2002 | Erickson |
| 6,423,063 B1 | 7/2002 | Bonutti |
| 6,425,920 B1 | 7/2002 | Hamada |
| 6,428,542 B1 | 8/2002 | Michelson |
| 6,428,575 B2 | 8/2002 | Koo et al. |
| 6,432,106 B1 | 8/2002 | Fraser |
| 6,432,107 B1 | 8/2002 | Ferree |
| 6,436,139 B1 | 8/2002 | Shapiro et al. |
| 6,436,140 B1 | 8/2002 | Liu et al. |
| 6,440,170 B1 | 8/2002 | Jackson |
| 6,443,989 B1 | 9/2002 | Jackson |
| 6,447,544 B1 | 9/2002 | Michelson |
| 6,447,547 B1 | 9/2002 | Michelson |
| 6,454,805 B1 | 9/2002 | Baccelli et al. |
| 6,454,806 B1 | 9/2002 | Cohen et al. |
| 6,454,807 B1 | 9/2002 | Jackson |
| 6,458,159 B1 | 10/2002 | Thalgott |
| 6,461,359 B1 | 10/2002 | Tribus |
| 6,471,724 B2 | 10/2002 | Zdeblick et al. |
| 6,478,823 B1 | 11/2002 | Michelson |
| 6,482,233 B1 | 11/2002 | Aebi et al. |
| 6,488,710 B2 | 12/2002 | Besselink |
| 6,491,724 B1 | 12/2002 | Ferree |
| 6,500,205 B1 | 12/2002 | Michelson |
| 6,517,580 B1 | 2/2003 | Ramadan et al. |
| 6,527,803 B1 | 3/2003 | Crozet et al. |
| 6,530,926 B1 | 3/2003 | Davison |
| 6,530,929 B1 | 3/2003 | Justis et al. |
| 6,558,424 B2 | 5/2003 | Thalgott |
| 6,562,041 B1 | 5/2003 | Yonemura et al. |
| 6,562,074 B2 | 5/2003 | Gerbec et al. |
| 6,576,016 B1 | 6/2003 | Hochshuler et al. |
| 6,582,431 B1 | 6/2003 | Ray |
| 6,582,437 B2 | 6/2003 | Dorchak et al. |
| 6,582,467 B1 | 6/2003 | Teitelbaum et al. |
| 6,592,586 B1 | 7/2003 | Michelson |
| 6,599,292 B1 | 7/2003 | Ray |
| 6,610,089 B1 | 8/2003 | Liu et al. |
| 6,613,091 B1 | 9/2003 | Zdeblick et al. |
| 6,616,695 B1 | 9/2003 | Crozet et al. |
| 6,641,614 B1 | 11/2003 | Wagner et al. |
| 6,645,206 B1 | 11/2003 | Zdeblick et al. |
| 6,648,915 B2 | 11/2003 | Sazy |
| 6,652,584 B2 | 11/2003 | Michelson |
| 6,660,038 B2 | 12/2003 | Boyer, II et al. |
| 6,666,888 B1 | 12/2003 | Jackson |
| 6,676,703 B2 | 1/2004 | Biscup |
| 6,685,742 B1 | 2/2004 | Jackson |
| 6,699,288 B2 | 3/2004 | Moret |
| 6,709,458 B2 | 3/2004 | Michelson |
| 6,716,247 B2 | 4/2004 | Michelson |
| 6,719,760 B2 | 4/2004 | Dorchak et al. |
| 6,719,794 B2 | 4/2004 | Gerber |
| 6,719,796 B2 | 4/2004 | Cohen et al. |
| 6,723,096 B1 | 4/2004 | Dorchak et al. |
| 6,723,126 B1 | 4/2004 | Berry |
| 6,726,722 B2 | 4/2004 | Walkenhorst et al. |
| 6,730,127 B2 | 5/2004 | Michelson |
| 6,740,093 B2 | 5/2004 | Hochschuler et al. |
| 6,743,255 B2 | 6/2004 | Ferree |
| 6,746,484 B1 | 6/2004 | Liu et al. |
| 6,767,366 B2 | 7/2004 | Lee et al. |
| 6,767,367 B1 | 7/2004 | Michelson |
| 6,770,096 B2 | 8/2004 | Bolger et al. |
| 6,773,460 B2 | 8/2004 | Jackson |
| 6,783,545 B2 | 8/2004 | Castro et al. |
| 6,793,679 B2 | 9/2004 | Michelson |
| RE38,614 E | 10/2004 | Paul et al. |
| 6,800,092 B1 | 10/2004 | Williams et al. |
| 6,800,093 B2 | 10/2004 | Nicholson et al. |
| 6,808,537 B2 | 10/2004 | Michelson |
| 6,814,756 B1 | 11/2004 | Michelson |
| 6,821,298 B1 | 11/2004 | Jackson |
| 6,824,564 B2 | 11/2004 | Crozet |
| 6,830,589 B2 | 12/2004 | Erickson |
| 6,835,206 B2 | 12/2004 | Jackson |
| 6,852,129 B2 | 2/2005 | Gerbec et al. |
| 6,855,166 B2 | 2/2005 | Kohrs |
| 6,855,168 B2 | 2/2005 | Crozet |
| 6,855,169 B2 | 2/2005 | Boyer, II et al. |
| 6,863,673 B2 | 3/2005 | Gerbec et al. |

(56) References Cited

U.S. PATENT DOCUMENTS

| | | |
|---|---|---|
| 6,890,355 B2 | 5/2005 | Michelson |
| 6,893,464 B2 | 5/2005 | Kiester |
| 6,893,465 B2 | 5/2005 | Huang |
| 6,899,716 B2 | 5/2005 | Cragg |
| 6,899,734 B2 | 5/2005 | Castro |
| 6,902,581 B2 | 6/2005 | Walkenhorst et al. |
| 6,916,320 B2 | 7/2005 | Michelson |
| 6,923,830 B2 | 8/2005 | Michelson |
| 6,926,737 B2 | 8/2005 | Jackson |
| 6,936,050 B2 | 8/2005 | Michelson |
| 6,936,051 B2 | 8/2005 | Michelson |
| 6,942,697 B2 | 9/2005 | Lange et al. |
| 6,942,698 B1 | 9/2005 | Jackson |
| 6,945,933 B2 | 9/2005 | Branch et al. |
| 6,953,477 B2 | 10/2005 | Berry |
| 6,955,691 B2 | 10/2005 | Chae et al. |
| 6,962,606 B2 | 11/2005 | Michelson |
| 6,969,390 B2 | 11/2005 | Michelson |
| 6,972,035 B2 | 12/2005 | Michelson |
| 6,974,480 B2 | 12/2005 | Messerli et al. |
| 7,008,422 B2 | 3/2006 | Foley et al. |
| 7,008,453 B1 | 3/2006 | Michelson |
| 7,014,659 B2 | 3/2006 | Boyer, II et al. |
| 7,018,414 B2 | 3/2006 | Brau et al. |
| 7,018,415 B1 | 3/2006 | McKay |
| 7,018,416 B2 | 3/2006 | Hanson et al. |
| 7,022,138 B2 | 4/2006 | Mashburn |
| 7,029,498 B2 | 4/2006 | Boehm et al. |
| 7,044,971 B2 | 5/2006 | Suddaby |
| 7,044,972 B2 | 5/2006 | Mathys, Jr. et al. |
| 7,056,321 B2 | 6/2006 | Pagliuca et al. |
| 7,060,073 B2 | 6/2006 | Frey et al. |
| 7,060,097 B2 | 6/2006 | Fraser et al. |
| 7,070,621 B2 | 7/2006 | Castro et al. |
| 7,087,058 B2 | 8/2006 | Cragg |
| 7,094,257 B2 | 8/2006 | Mujwid et al. |
| 7,105,023 B2 | 9/2006 | Eckman |
| 7,105,025 B2 | 9/2006 | Castro et al. |
| 7,112,206 B2 | 9/2006 | Michelson |
| 7,112,222 B2 | 9/2006 | Fraser et al. |
| 7,112,224 B2 | 9/2006 | Liu et al. |
| 7,118,598 B2 | 10/2006 | Michelson |
| 7,125,424 B2 | 10/2006 | Banick et al. |
| 7,128,760 B2 | 10/2006 | Michelson |
| 7,128,762 B2 | 10/2006 | Middleton |
| 7,137,997 B2 | 11/2006 | Paul |
| 7,156,874 B2 | 1/2007 | Paponneau et al. |
| 7,156,875 B2 | 1/2007 | Michelson |
| 7,166,129 B2 | 1/2007 | Michelson |
| 7,179,293 B2 | 2/2007 | McKay |
| 7,182,782 B2 | 2/2007 | Kirschman |
| 7,192,446 B2 | 3/2007 | Shapiro et al. |
| 7,192,447 B2 | 3/2007 | Rhoda |
| 7,195,643 B2 | 3/2007 | Jackson |
| 7,201,775 B2 | 4/2007 | Gorensek et al. |
| 7,207,949 B2 | 4/2007 | Miles et al. |
| 7,214,243 B2 | 5/2007 | Taylor |
| 7,217,293 B2 | 5/2007 | Branch, Jr. |
| 7,220,282 B2 | 5/2007 | Kuslich |
| 7,223,292 B2 | 5/2007 | Messerli et al. |
| 7,226,480 B2 | 6/2007 | Thalgott |
| 7,226,483 B2 | 6/2007 | Gerber et al. |
| 7,229,477 B2 | 6/2007 | Biscup |
| 7,232,463 B2 | 6/2007 | Falahee |
| 7,235,105 B2 | 6/2007 | Jackson |
| 7,238,186 B2 | 7/2007 | Zdeblick et al. |
| 7,238,203 B2 | 7/2007 | Bagga et al. |
| 7,238,206 B2 | 7/2007 | Lange et al. |
| 7,285,134 B2 | 10/2007 | Berry et al. |
| 7,285,135 B2 | 10/2007 | McKay et al. |
| 7,303,583 B1 | 12/2007 | Schär et al. |
| 7,303,584 B2 | 12/2007 | Castro et al. |
| 7,316,686 B2 | 1/2008 | Dorchak et al. |
| 7,316,714 B2 | 1/2008 | Gordon et al. |
| 7,326,248 B2 | 2/2008 | Michelson |
| D564,095 S | 3/2008 | Blain |
| 7,361,193 B2 | 4/2008 | Frey et al. |
| 7,384,431 B2 | 6/2008 | Berry |
| 7,396,365 B2 | 7/2008 | Michelson |
| 7,402,176 B2 | 7/2008 | Malek |
| 7,410,501 B2 | 8/2008 | Michelson |
| 7,431,735 B2 | 10/2008 | Liu et al. |
| 7,435,261 B1 | 10/2008 | Castro |
| 7,445,636 B2 | 11/2008 | Michelson |
| 7,455,672 B2 | 11/2008 | Michelson |
| 7,455,692 B2 | 11/2008 | Michelson |
| 7,462,196 B2 | 12/2008 | Fraser |
| 7,465,305 B2 | 12/2008 | Liu et al. |
| 7,470,236 B1 | 12/2008 | Kelleher et al. |
| 7,470,273 B2 | 12/2008 | Dougherty-Shah |
| 7,473,276 B2 | 1/2009 | Aebi et al. |
| 7,473,277 B2 | 1/2009 | Boyer, II et al. |
| 7,476,251 B2 | 1/2009 | Zucherman et al. |
| 7,481,766 B2 | 1/2009 | Lee et al. |
| 7,485,120 B2 | 2/2009 | Ray |
| 7,500,991 B2 | 3/2009 | Bartish, Jr. et al. |
| 7,503,933 B2 | 3/2009 | Michelson |
| 7,509,183 B2 | 3/2009 | Lin et al. |
| 7,534,254 B1 | 5/2009 | Michelson |
| 7,540,882 B2 | 6/2009 | Michelson |
| 7,544,208 B1 | 6/2009 | Mueller et al. |
| 7,569,074 B2 | 8/2009 | Eisermann et al. |
| 7,575,601 B2 | 8/2009 | Dickson |
| 7,582,058 B1 | 9/2009 | Miles et al. |
| 7,588,599 B2 | 9/2009 | Sweeney |
| 7,591,852 B2 | 9/2009 | Prosser |
| 7,594,931 B2 | 9/2009 | Louis et al. |
| 7,608,105 B2 | 10/2009 | Pavlov et al. |
| 7,608,107 B2 | 10/2009 | Michelson |
| 7,618,454 B2 | 11/2009 | Bentley et al. |
| 7,621,938 B2 | 11/2009 | Molz |
| 7,621,950 B1 | 11/2009 | Globerman et al. |
| 7,621,960 B2 | 11/2009 | Boyd et al. |
| 7,637,953 B2 | 12/2009 | Branch et al. |
| 7,641,690 B2 | 1/2010 | Abdou |
| 7,655,010 B2 | 2/2010 | Serhan et al. |
| 7,655,027 B2 | 2/2010 | Michelson |
| 7,655,043 B2 | 2/2010 | Peterman et al. |
| 7,655,046 B2 | 2/2010 | Dryer et al. |
| 7,662,186 B2 | 2/2010 | Bagga et al. |
| 7,670,359 B2 | 3/2010 | Yundt |
| 7,674,296 B2 | 3/2010 | Rhoda et al. |
| 7,674,297 B2 | 3/2010 | Falahee |
| 7,678,148 B2 | 3/2010 | Peterman |
| 7,682,394 B2 | 3/2010 | Recoules-Arche et al. |
| 7,695,515 B2 | 4/2010 | Sweeney |
| 7,708,778 B2 | 5/2010 | Gordon et al. |
| 7,713,302 B2 | 5/2010 | Ralph et al. |
| 7,722,674 B1 | 5/2010 | Grotz |
| 7,723,395 B2 | 5/2010 | Ringelsen et al. |
| 7,727,280 B2 | 6/2010 | McLuen |
| 7,731,751 B2 | 6/2010 | Butler et al. |
| 7,749,270 B2 | 7/2010 | Peterman |
| 7,753,958 B2 | 7/2010 | Gordon et al. |
| 7,758,644 B2 | 7/2010 | Trieu |
| 7,763,079 B2 | 7/2010 | McKay |
| 7,771,473 B2 | 8/2010 | Thramann |
| 7,776,093 B2 | 8/2010 | Wolek et al. |
| 7,776,095 B2 | 8/2010 | Peterman et al. |
| 7,780,732 B2 | 8/2010 | Abernathie |
| 7,799,081 B2 | 9/2010 | McKinley |
| 7,803,191 B2 | 9/2010 | Biedermann et al. |
| 7,811,327 B2 | 10/2010 | Hansell et al. |
| 7,819,921 B2 | 10/2010 | Grotz |
| 7,824,427 B2 | 11/2010 | Perez-Cruet et al. |
| 7,824,445 B2 | 11/2010 | Biro et al. |
| 7,828,848 B2 | 11/2010 | Chauvin et al. |
| 7,837,732 B2 | 11/2010 | Zucherman et al. |
| 7,837,735 B2 | 11/2010 | Malone |
| 7,846,210 B2 | 12/2010 | Perez-Cruet |
| 7,850,733 B2 | 12/2010 | Baynham et al. |
| 7,850,734 B2 | 12/2010 | Oh et al. |
| 7,850,736 B2 | 12/2010 | Heinz |
| 7,875,075 B2 | 1/2011 | Schwab |

(56) References Cited

U.S. PATENT DOCUMENTS

| | | | |
|---|---|---|---|
| 7,875,078 B2 | 1/2011 | Wysocki et al. |
| 7,879,098 B1 | 2/2011 | Simmons, Jr. |
| 7,887,596 B2 | 2/2011 | Douget et al. |
| 7,892,286 B2 | 2/2011 | Michelson |
| 7,914,581 B2 | 3/2011 | Dickson et al. |
| 7,922,729 B2 | 4/2011 | Michelson |
| 7,951,180 B2 | 5/2011 | Moskowitz et al. |
| 7,951,199 B2 | 5/2011 | Miller |
| 7,967,863 B2 | 6/2011 | Frey et al. |
| 7,967,867 B2 | 6/2011 | Barreiro et al. |
| 7,981,156 B2 | 7/2011 | Pafford et al. |
| 7,985,256 B2 | 7/2011 | Grotz et al. |
| 7,985,258 B2 | 7/2011 | Zdeblick et al. |
| 8,002,832 B2 | 8/2011 | Castro |
| 8,002,833 B2 | 8/2011 | Fabris Monterumici et al. |
| 8,007,534 B2 | 8/2011 | Michelson |
| 8,016,887 B1 | 9/2011 | Castro |
| 8,034,110 B2 | 10/2011 | Garner et al. |
| 8,034,111 B2 | 10/2011 | Hsu et al. |
| 8,043,376 B2 | 10/2011 | Falahee |
| 8,043,377 B2 | 10/2011 | Guyer et al. |
| 8,057,548 B2 | 11/2011 | Abernathie et al. |
| 8,062,366 B2 | 11/2011 | Melkent |
| 8,062,368 B2 | 11/2011 | Heinz et al. |
| 8,062,375 B2 | 11/2011 | Glerum et al. |
| 8,070,812 B2 | 12/2011 | Keller |
| 8,070,813 B2 | 12/2011 | Grotz |
| 8,070,816 B2 | 12/2011 | Taylor |
| 8,075,621 B2 | 12/2011 | Michelson |
| 8,083,744 B2 | 12/2011 | Dorchak et al. |
| 8,083,799 B2 | 12/2011 | Baynham et al. |
| 8,088,163 B1 | 1/2012 | Kleiner |
| 8,097,034 B2 | 1/2012 | Michelson |
| 8,100,972 B1 | 1/2012 | Bruffey et al. |
| 8,105,382 B2 | 1/2012 | Olmos et al. |
| 8,110,004 B2 | 2/2012 | Valdevit et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,128,700 B2 | 3/2012 | Delurio et al. |
| 8,137,401 B2 | 3/2012 | Stad et al. |
| 8,142,503 B2 | 3/2012 | Malone |
| 8,142,508 B1 | 3/2012 | Bruffey et al. |
| RE43,317 E | 4/2012 | Fraser et al. |
| 8,147,550 B2 | 4/2012 | Gordon et al. |
| 8,147,556 B2 | 4/2012 | Louis et al. |
| 8,152,851 B2 | 4/2012 | Mueller et al. |
| 8,152,852 B2 | 4/2012 | Biyani |
| 8,157,865 B2 | 4/2012 | Hochschuler et al. |
| 8,167,946 B2 | 5/2012 | Michelson |
| 8,172,903 B2 | 5/2012 | Gordon et al. |
| 8,172,905 B2 | 5/2012 | Baynham et al. |
| 8,177,844 B2 | 5/2012 | Tsuang et al. |
| 8,177,848 B2 | 5/2012 | McKay |
| 8,182,535 B2 | 5/2012 | Kraus |
| 8,182,538 B2 | 5/2012 | O'Neil et al. |
| 8,187,304 B2 | 5/2012 | Malek |
| 8,187,331 B2 | 5/2012 | Strohkirch, Jr. et al. |
| 8,187,332 B2 | 5/2012 | McLuen |
| 8,192,357 B2 * | 6/2012 | Miles et al. ............ 600/202 |
| 8,192,495 B2 | 6/2012 | Simpson et al. |
| 8,197,546 B2 | 6/2012 | Doubler et al. |
| 8,221,501 B2 | 7/2012 | Eisermann et al. |
| 8,221,502 B2 | 7/2012 | Branch, Jr. |
| 8,226,718 B2 | 7/2012 | Castro |
| 8,241,294 B2 | 8/2012 | Sommerich et al. |
| 8,241,358 B2 | 8/2012 | Butler et al. |
| 8,241,359 B2 | 8/2012 | Davis et al. |
| 8,241,363 B2 | 8/2012 | Sommerich et al. |
| 8,246,683 B2 | 8/2012 | Castro |
| 8,252,059 B2 | 8/2012 | Overes et al. |
| 8,257,436 B2 | 9/2012 | Jackson |
| 8,257,440 B2 | 9/2012 | Gordon et al. |
| 8,257,442 B2 | 9/2012 | Edie et al. |
| 8,262,737 B2 | 9/2012 | Bagga et al. |
| 8,273,124 B2 | 9/2012 | Renganath et al. |
| 8,273,128 B2 | 9/2012 | Oh et al. |
| 8,277,510 B2 | 10/2012 | Kleiner |
| 8,282,683 B2 | 10/2012 | McLaughlin et al. |
| 8,287,599 B2 | 10/2012 | McGuckin, Jr. |
| 8,292,928 B2 | 10/2012 | Cragg et al. |
| 8,292,958 B1 | 10/2012 | Bruffey et al. |
| 8,292,960 B2 | 10/2012 | Kleiner |
| 8,292,963 B2 | 10/2012 | Miller et al. |
| 8,303,658 B2 | 11/2012 | Peterman |
| 8,303,662 B2 | 11/2012 | Landry et al. |
| 8,303,663 B2 | 11/2012 | Jimenez et al. |
| 8,303,879 B2 | 11/2012 | Bertele et al. |
| 8,308,802 B2 | 11/2012 | Rhoda et al. |
| 8,308,805 B2 | 11/2012 | Lynn et al. |
| 8,323,341 B2 | 12/2012 | Lambrecht et al. |
| 8,323,345 B2 | 12/2012 | Sledge |
| 8,333,804 B1 | 12/2012 | Wensel |
| 8,337,558 B2 | 12/2012 | Lindner |
| 8,337,559 B2 | 12/2012 | Hansell et al. |
| 8,343,224 B2 | 1/2013 | Lynn et al. |
| 8,353,961 B2 | 1/2013 | McClintock et al. |
| 8,361,149 B2 | 1/2013 | Castro |
| 8,361,153 B2 | 1/2013 | Ralph et al. |
| 8,366,774 B1 | 2/2013 | Bruffey et al. |
| 8,372,151 B2 | 2/2013 | Hsu et al. |
| 8,377,132 B2 | 2/2013 | Wing et al. |
| 8,377,139 B2 | 2/2013 | Laubert et al. |
| 8,382,841 B2 | 2/2013 | Yundt |
| 8,382,842 B2 | 2/2013 | Greenhalgh et al. |
| 8,388,667 B2 | 3/2013 | Reiley et al. |
| 8,394,143 B2 | 3/2013 | Grotz et al. |
| 8,398,713 B2 | 3/2013 | Weiman |
| 8,403,990 B2 | 3/2013 | Dryer et al. |
| 8,403,991 B2 | 3/2013 | Ullrich, Jr. et al. |
| 8,409,285 B2 | 4/2013 | Keller |
| 8,409,286 B2 | 4/2013 | McKay |
| 8,409,287 B2 | 4/2013 | Braddock, Jr. et al. |
| 8,409,288 B2 | 4/2013 | Davis et al. |
| 8,414,651 B2 | 4/2013 | Tyber et al. |
| 8,419,795 B2 | 4/2013 | Sweeney |
| 8,419,797 B2 | 4/2013 | Biedermann et al. |
| 8,425,612 B2 | 4/2013 | Perez-Cruet |
| 8,430,930 B2 | 4/2013 | Hunt |
| 8,435,296 B2 | 5/2013 | Kadaba et al. |
| 8,435,298 B2 | 5/2013 | Weiman |
| 8,435,299 B2 | 5/2013 | Chauvin et al. |
| 8,435,300 B2 | 5/2013 | Messerli et al. |
| 8,435,302 B2 | 5/2013 | Ulrich, Jr. et al. |
| 8,444,692 B2 | 5/2013 | Michelson |
| 8,449,613 B2 | 5/2013 | Crozet |
| 8,454,695 B2 | 6/2013 | Grotz et al. |
| 8,460,385 B1 | 6/2013 | Wensel |
| 8,475,533 B1 | 7/2013 | Castro |
| 8,480,741 B2 | 7/2013 | Grotz et al. |
| 8,480,745 B2 | 7/2013 | Liu et al. |
| 8,480,748 B2 | 7/2013 | Poulos |
| 8,480,749 B2 | 7/2013 | Ullrich, Jr. et al. |
| 8,486,148 B2 | 7/2013 | Butler et al. |
| 8,486,149 B2 | 7/2013 | Saidha et al. |
| 8,491,653 B2 | 7/2013 | Zucherman et al. |
| 8,491,657 B2 | 7/2013 | Attia et al. |
| 8,491,659 B2 | 7/2013 | Weiman |
| 8,496,706 B2 | 7/2013 | Ragab et al. |
| 8,496,710 B2 | 7/2013 | Bagga et al. |
| RE44,417 E | 8/2013 | Bartish, Jr. et al. |
| 8,506,629 B2 | 8/2013 | Weiland |
| 8,512,407 B2 | 8/2013 | Butler et al. |
| 8,518,120 B2 | 8/2013 | Glerum et al. |
| 8,523,908 B2 | 9/2013 | Malone |
| 8,523,909 B2 | 9/2013 | Hess |
| 8,523,944 B2 | 9/2013 | Jimenez et al. |
| 8,535,380 B2 | 9/2013 | Greenhalgh et al. |
| 8,540,770 B2 | 9/2013 | Woodburn, Sr. |
| 8,545,568 B2 | 10/2013 | Ulrich, Jr. et al. |
| 8,551,176 B2 | 10/2013 | Ullrich, Jr. et al. |
| 8,556,979 B2 | 10/2013 | Glerum et al. |
| 8,562,683 B2 | 10/2013 | McKinley |
| 8,562,684 B2 | 10/2013 | Ullrich, Jr. et al. |

(56) References Cited

U.S. PATENT DOCUMENTS

| | | |
|---|---|---|
| 8,562,685 B2 | 10/2013 | Ullrich, Jr. et al. |
| 8,568,481 B2 | 10/2013 | Olmos et al. |
| 8,568,482 B2 | 10/2013 | Kraus et al. |
| 8,574,297 B2 | 11/2013 | Stad et al. |
| 8,574,299 B2 | 11/2013 | Barreiro et al. |
| 8,574,300 B2 | 11/2013 | McManus et al. |
| 8,579,976 B2 | 11/2013 | Attia |
| 8,579,979 B2 | 11/2013 | Edie et al. |
| 8,579,983 B2 | 11/2013 | Garner et al. |
| 8,585,761 B2 | 11/2013 | Theofilos |
| 8,585,765 B2 | 11/2013 | Ullrich, Jr. et al. |
| 8,585,766 B2 | 11/2013 | Ullrich, Jr. et al. |
| 8,585,767 B2 | 11/2013 | Ullrich, Jr. et al. |
| 8,591,585 B2 | 11/2013 | McLaughlin et al. |
| 8,591,588 B2 | 11/2013 | Fraser et al. |
| 8,591,590 B2 | 11/2013 | Ullrich, Jr. et al. |
| 8,597,360 B2 | 12/2013 | McLuen et al. |
| 8,603,170 B2 | 12/2013 | Cipoletti et al. |
| 8,603,174 B2 | 12/2013 | Haines |
| 8,617,246 B2 | 12/2013 | Malone |
| 8,617,248 B2 | 12/2013 | Ullrich, Jr. et al. |
| 8,628,575 B2 | 1/2014 | Muhanna et al. |
| 8,628,576 B2 | 1/2014 | Triplett et al. |
| 8,632,595 B2 | 1/2014 | Weiman |
| 8,641,763 B2 | 2/2014 | Yue |
| 8,641,765 B2 | 2/2014 | Muhanna |
| 8,641,769 B2 | 2/2014 | Malandain |
| 8,647,386 B2 | 2/2014 | Gordon et al. |
| 8,663,329 B2 | 3/2014 | Ernst |
| 8,663,330 B2 | 3/2014 | McClintock et al. |
| 8,663,331 B2 | 3/2014 | McClellan, III et al. |
| 8,668,740 B2 | 3/2014 | Rhoda et al. |
| 8,668,741 B2 | 3/2014 | Michelson |
| 8,673,004 B2 | 3/2014 | Michelson |
| 8,673,006 B2 | 3/2014 | Castro |
| 8,673,011 B2 | 3/2014 | Theofilos et al. |
| 8,673,012 B2 | 3/2014 | Smith et al. |
| 8,679,183 B2 | 3/2014 | Glerum et al. |
| 8,679,184 B2 | 3/2014 | Kube, II |
| 8,685,031 B2 | 4/2014 | Kleiner et al. |
| 8,685,095 B2 | 4/2014 | Miller et al. |
| 8,685,098 B2 | 4/2014 | Glerum et al. |
| 8,685,102 B2 | 4/2014 | McKay |
| 8,685,104 B2 | 4/2014 | Lee et al. |
| 8,690,949 B2 | 4/2014 | Messerli et al. |
| 8,696,751 B2 | 4/2014 | Ashley et al. |
| 8,696,752 B2 | 4/2014 | Shih et al. |
| 8,709,042 B2 | 4/2014 | Greenhalgh et al. |
| 8,709,083 B2 | 4/2014 | Duffield et al. |
| 8,709,086 B2 | 4/2014 | Glerum |
| 8,715,351 B1 | 5/2014 | Pinto |
| 8,715,353 B2 | 5/2014 | Bagga et al. |
| 8,715,355 B2 | 5/2014 | Kleiner |
| 8,721,723 B2 | 5/2014 | Hansell et al. |
| 8,728,160 B2 | 5/2014 | Globerman et al. |
| 8,734,447 B1 | 5/2014 | Michaelson |
| 8,734,519 B2 | 5/2014 | de Villiers |
| 8,734,521 B2 | 5/2014 | Freeman et al. |
| 8,734,822 B2 | 5/2014 | Koblish et al. |
| 8,753,398 B2 | 6/2014 | Gordon et al. |
| 8,753,399 B2 | 6/2014 | Sharifi-Mehr |
| 8,771,358 B2 | 7/2014 | Michelson |
| 8,771,360 B2 | 7/2014 | Jimenez et al. |
| 8,771,368 B2 | 7/2014 | McKay |
| 8,778,025 B2 | 7/2014 | Ragab et al. |
| 8,778,027 B2 | 7/2014 | Medina |
| 8,808,305 B2 | 8/2014 | Kleiner |
| 8,808,385 B1 | 8/2014 | Smith et al. |
| 8,834,571 B2 | 9/2014 | Bagga et al. |
| 8,840,620 B2 | 9/2014 | Recoules-Arche et al. |
| 8,840,666 B2 | 9/2014 | Crozet |
| 8,840,669 B2 | 9/2014 | Farris et al. |
| 8,845,733 B2 | 9/2014 | O'Neil et al. |
| 8,852,278 B2 | 10/2014 | Bellasw |
| 2001/0001129 A1 | 5/2001 | McKay et al. |
| 2001/0010020 A1 | 7/2001 | Michelson |
| 2001/0047208 A1 | 11/2001 | Michelson |
| 2001/0051829 A1 | 12/2001 | Middleton |
| 2002/0040243 A1 | 4/2002 | Attali et al. |
| 2002/0045945 A1 | 4/2002 | Liu et al. |
| 2002/0049394 A1 | 4/2002 | Roy et al. |
| 2002/0082697 A1 | 6/2002 | Damien |
| 2002/0103540 A1 | 8/2002 | Cooper et al. |
| 2002/0111684 A1 | 8/2002 | Ralph et al. |
| 2002/0111687 A1 | 8/2002 | Ralph et al. |
| 2002/0123750 A1 | 9/2002 | Eisermann et al. |
| 2002/0128652 A1 | 9/2002 | Ferree |
| 2002/0128712 A1 | 9/2002 | Michelson |
| 2002/0138146 A1 | 9/2002 | Jackson |
| 2002/0138147 A1 | 9/2002 | Cohen |
| 2002/0143401 A1 | 10/2002 | Michelson |
| 2002/0161444 A1 | 10/2002 | Choi |
| 2002/0169507 A1 | 11/2002 | Malone |
| 2002/0193880 A1 | 12/2002 | Fraser |
| 2002/0198598 A1 | 12/2002 | Pepper |
| 2003/0069640 A1 | 4/2003 | Ferreira et al. |
| 2003/0083746 A1 | 5/2003 | Kuslich |
| 2003/0083748 A1 | 5/2003 | Lee et al. |
| 2003/0105527 A1 | 6/2003 | Bresina |
| 2003/0114854 A1 | 6/2003 | Pavlov et al. |
| 2003/0114930 A1 | 6/2003 | Lim et al. |
| 2003/0171812 A1 | 9/2003 | Grunberg et al. |
| 2003/0171813 A1 | 9/2003 | Kiester |
| 2003/0181979 A1 | 9/2003 | Ferree |
| 2003/0195520 A1 | 10/2003 | Boyd et al. |
| 2003/0208275 A1 | 11/2003 | Michelson |
| 2004/0034421 A1 | 2/2004 | Errico et al. |
| 2004/0034430 A1 | 2/2004 | Falahee |
| 2004/0059420 A1 | 3/2004 | Michelson |
| 2004/0073314 A1 | 4/2004 | White et al. |
| 2004/0082953 A1 | 4/2004 | Petit |
| 2004/0122424 A1 | 6/2004 | Ferree |
| 2004/0127993 A1 | 7/2004 | Kast et al. |
| 2004/0143330 A1 | 7/2004 | Sazy |
| 2004/0153160 A1 | 8/2004 | Carrasco |
| 2004/0186483 A1 | 9/2004 | Bagby |
| 2004/0220670 A1 | 11/2004 | Eisermann et al. |
| 2004/0220671 A1 | 11/2004 | Ralph et al. |
| 2004/0249461 A1 | 12/2004 | Ferree |
| 2004/0254643 A1 | 12/2004 | Jackson |
| 2004/0254644 A1 | 12/2004 | Taylor |
| 2005/0027362 A1 | 2/2005 | Williams et al. |
| 2005/0033431 A1 | 2/2005 | Gordon et al. |
| 2005/0033432 A1 | 2/2005 | Gordon et al. |
| 2005/0033439 A1 | 2/2005 | Gordon et al. |
| 2005/0043802 A1 | 2/2005 | Eisermann et al. |
| 2005/0049587 A1 | 3/2005 | Jackson |
| 2005/0049590 A1 | 3/2005 | Alleyne et al. |
| 2005/0065605 A1 | 3/2005 | Jackson |
| 2005/0065611 A1 | 3/2005 | Huppert et al. |
| 2005/0070900 A1 | 3/2005 | Serhan et al. |
| 2005/0080320 A1* | 4/2005 | Lee et al. .................. 600/214 |
| 2005/0119751 A1 | 6/2005 | Lawson |
| 2005/0119753 A1 | 6/2005 | McGahan et al. |
| 2005/0131548 A1 | 6/2005 | Boyer et al. |
| 2005/0149192 A1 | 7/2005 | Zuckerman et al. |
| 2005/0159816 A1 | 7/2005 | Walkenhorst et al. |
| 2005/0177173 A1 | 8/2005 | Aebi et al. |
| 2005/0177237 A1 | 8/2005 | Shappley et al. |
| 2005/0192669 A1 | 9/2005 | Zdeblick et al. |
| 2005/0209697 A1 | 9/2005 | Paponneau et al. |
| 2005/0216082 A1 | 9/2005 | Wilson et al. |
| 2005/0216089 A1 | 9/2005 | Michelson |
| 2005/0222681 A1 | 10/2005 | Richley et al. |
| 2005/0278027 A1 | 12/2005 | Hyde |
| 2005/0283245 A1 | 12/2005 | Gordon et al. |
| 2005/0283248 A1 | 12/2005 | Gordon et al. |
| 2006/0041314 A1 | 2/2006 | Millard |
| 2006/0047341 A1 | 3/2006 | Trieu |
| 2006/0064170 A1 | 3/2006 | Smith et al. |
| 2006/0084985 A1 | 4/2006 | Kim |
| 2006/0095136 A1 | 5/2006 | McLuen |
| 2006/0116767 A1 | 6/2006 | Magerl et al. |
| 2006/0122701 A1 | 6/2006 | Kiester |

(56) References Cited

U.S. PATENT DOCUMENTS

| | | |
|---|---|---|
| 2006/0122703 A1 | 6/2006 | Aebi et al. |
| 2006/0173543 A1 | 8/2006 | Brau et al. |
| 2006/0190081 A1 | 8/2006 | Kraus et al. |
| 2006/0195192 A1 | 8/2006 | Gordon et al. |
| 2006/0224241 A1 | 10/2006 | Butler et al. |
| 2006/0229729 A1 | 10/2006 | Gordon et al. |
| 2006/0241774 A1 | 10/2006 | Attali et al. |
| 2007/0050029 A1 | 3/2007 | Carrasco |
| 2007/0050030 A1 | 3/2007 | Kim |
| 2007/0055252 A1 | 3/2007 | Blain et al. |
| 2007/0067035 A1 | 3/2007 | Falahee |
| 2007/0073291 A1 | 3/2007 | Cordaro et al. |
| 2007/0073400 A1 | 3/2007 | Paul |
| 2007/0073406 A1 | 3/2007 | Gordon et al. |
| 2007/0118222 A1 | 5/2007 | Lang |
| 2007/0168038 A1 | 7/2007 | Trieu |
| 2007/0168039 A1 | 7/2007 | Trieu |
| 2007/0185580 A1 | 8/2007 | Posel |
| 2007/0191951 A1 | 8/2007 | Branch |
| 2007/0225810 A1 | 9/2007 | Colleran et al. |
| 2007/0233254 A1 | 10/2007 | Grotz et al. |
| 2007/0233263 A1 | 10/2007 | Melkent |
| 2007/0244485 A1 | 10/2007 | Greenhalgh et al. |
| 2007/0260314 A1 | 11/2007 | Biyani |
| 2007/0276377 A1 | 11/2007 | Yundt |
| 2007/0282171 A1* | 12/2007 | Karpowicz ............... A61B 1/32 600/224 |
| 2007/0282443 A1 | 12/2007 | Globerman et al. |
| 2007/0293948 A1 | 12/2007 | Bagga et al. |
| 2007/0293949 A1 | 12/2007 | Salerni et al. |
| 2008/0009880 A1 | 1/2008 | Warnick et al. |
| 2008/0015701 A1 | 1/2008 | Garcia et al. |
| 2008/0021462 A1 | 1/2008 | Trieu |
| 2008/0021556 A1 | 1/2008 | Edie |
| 2008/0021559 A1 | 1/2008 | Thramann |
| 2008/0039948 A1 | 2/2008 | Biedermann et al. |
| 2008/0051902 A1 | 2/2008 | Dwyer |
| 2008/0051903 A1 | 2/2008 | Dwyer |
| 2008/0058931 A1 | 3/2008 | White et al. |
| 2008/0065217 A1 | 3/2008 | Hurlbert et al. |
| 2008/0065219 A1 | 3/2008 | Dye et al. |
| 2008/0071284 A1 | 3/2008 | Lechmann et al. |
| 2008/0077247 A1 | 3/2008 | Murillo et al. |
| 2008/0091211 A1 | 4/2008 | Gately |
| 2008/0091270 A1 | 4/2008 | Miller et al. |
| 2008/0097610 A1 | 4/2008 | Guyer et al. |
| 2008/0114454 A1 | 5/2008 | Peterman et al. |
| 2008/0133015 A1 | 6/2008 | Lechmann et al. |
| 2008/0147194 A1 | 6/2008 | Grotz et al. |
| 2008/0154374 A1 | 6/2008 | Labrom |
| 2008/0154377 A1 | 6/2008 | Voellmicke |
| 2008/0161927 A1 | 7/2008 | Savage et al. |
| 2008/0161933 A1 | 7/2008 | Grotz et al. |
| 2008/0172127 A1 | 7/2008 | Perez-Cruet et al. |
| 2008/0172128 A1 | 7/2008 | Perez Cruet et al. |
| 2008/0177387 A1 | 7/2008 | Parimore et al. |
| 2008/0195209 A1 | 8/2008 | Garcia et al. |
| 2008/0208345 A1 | 8/2008 | Hurlbert et al. |
| 2008/0215093 A1 | 9/2008 | Lin et al. |
| 2008/0221694 A1 | 9/2008 | Warnick et al. |
| 2008/0221695 A1 | 9/2008 | Jacofsky et al. |
| 2008/0243252 A1 | 10/2008 | Hansen et al. |
| 2008/0249622 A1 | 10/2008 | Gray |
| 2008/0249627 A1 | 10/2008 | Moehlenbruck et al. |
| 2008/0262623 A1 | 10/2008 | Bagga et al. |
| 2008/0269901 A1 | 10/2008 | Baynham et al. |
| 2008/0269902 A1 | 10/2008 | Baynham et al. |
| 2008/0281424 A1 | 11/2008 | Parry et al. |
| 2008/0288071 A1 | 11/2008 | Biyani et al. |
| 2008/0288076 A1 | 11/2008 | Soo et al. |
| 2008/0312742 A1 | 12/2008 | Abernathie |
| 2009/0005870 A1 | 1/2009 | Hawkins et al. |
| 2009/0012620 A1 | 1/2009 | Youssef et al. |
| 2009/0024218 A1 | 1/2009 | Frigg et al. |
| 2009/0030519 A1 | 1/2009 | Falahee |
| 2009/0036985 A1 | 2/2009 | Whiting |
| 2009/0043394 A1 | 2/2009 | Zdeblick et al. |
| 2009/0054983 A1 | 2/2009 | Wuisman et al. |
| 2009/0054987 A1 | 2/2009 | Chin et al. |
| 2009/0054991 A1 | 2/2009 | Biyani et al. |
| 2009/0062917 A1 | 3/2009 | Foley et al. |
| 2009/0080997 A1 | 3/2009 | Johnson |
| 2009/0082775 A1 | 3/2009 | Altarac et al. |
| 2009/0088765 A1 | 4/2009 | Butler et al. |
| 2009/0088849 A1 | 4/2009 | Armstrong et al. |
| 2009/0099659 A1 | 4/2009 | Oh et al. |
| 2009/0105830 A1 | 4/2009 | Jones et al. |
| 2009/0105832 A1 | 4/2009 | Allain et al. |
| 2009/0125066 A1 | 5/2009 | Kraus et al. |
| 2009/0132053 A1 | 5/2009 | Sears et al. |
| 2009/0138083 A1 | 5/2009 | Biyani |
| 2009/0138091 A1 | 5/2009 | Ray |
| 2009/0143860 A1 | 6/2009 | Burd et al. |
| 2009/0149957 A1 | 6/2009 | Burd et al. |
| 2009/0157187 A1 | 6/2009 | Richelsoph |
| 2009/0164015 A1 | 6/2009 | Liu et al. |
| 2009/0164017 A1 | 6/2009 | Sommerich et al. |
| 2009/0164018 A1 | 6/2009 | Sommerich et al. |
| 2009/0164019 A1 | 6/2009 | Hsu et al. |
| 2009/0182428 A1 | 7/2009 | McClellan, III et al. |
| 2009/0182430 A1 | 7/2009 | Tyber et al. |
| 2009/0182431 A1 | 7/2009 | Butler et al. |
| 2009/0192613 A1 | 7/2009 | Wing et al. |
| 2009/0198338 A1 | 8/2009 | Phan |
| 2009/0198339 A1 | 8/2009 | Kleiner et al. |
| 2009/0203969 A1* | 8/2009 | Cohen ................... A61B 17/02 600/245 |
| 2009/0210061 A1 | 8/2009 | Sledge |
| 2009/0210062 A1 | 8/2009 | Thalgott et al. |
| 2009/0216331 A1 | 8/2009 | Grotz et al. |
| 2009/0234277 A1 | 9/2009 | Wei et al. |
| 2009/0248163 A1 | 10/2009 | King et al. |
| 2009/0265007 A1 | 10/2009 | Colleran |
| 2009/0276049 A1 | 11/2009 | Weiland |
| 2009/0299478 A1 | 12/2009 | Carls et al. |
| 2009/0299479 A1 | 12/2009 | Jones et al. |
| 2009/0326657 A1 | 12/2009 | Grinberg et al. |
| 2010/0004747 A1 | 1/2010 | Lin |
| 2010/0010633 A1 | 1/2010 | Kohm |
| 2010/0042219 A1 | 2/2010 | Antonacci et al. |
| 2010/0049325 A1 | 2/2010 | Biedermann et al. |
| 2010/0057207 A1 | 3/2010 | Ray et al. |
| 2010/0063510 A1 | 3/2010 | Arlet et al. |
| 2010/0070036 A1 | 3/2010 | Implicito |
| 2010/0070037 A1 | 3/2010 | Parry et al. |
| 2010/0070041 A1 | 3/2010 | Peterman et al. |
| 2010/0076559 A1 | 3/2010 | Bagga et al. |
| 2010/0087924 A1 | 4/2010 | Arlet |
| 2010/0106250 A1 | 4/2010 | Abdou |
| 2010/0114105 A1 | 5/2010 | Butters et al. |
| 2010/0145455 A1 | 6/2010 | Simpson et al. |
| 2010/0161057 A1 | 6/2010 | Berry et al. |
| 2010/0168798 A1 | 7/2010 | Clineff et al. |
| 2010/0174146 A1* | 7/2010 | Miles et al. .................. 600/202 |
| 2010/0179594 A1 | 7/2010 | Theofilos et al. |
| 2010/0179658 A1 | 7/2010 | Freeman et al. |
| 2010/0185289 A1 | 7/2010 | Kirwan et al. |
| 2010/0191336 A1 | 7/2010 | Greenhalgh |
| 2010/0204795 A1 | 8/2010 | Greenhalgh |
| 2010/0222884 A1 | 9/2010 | Greenhalgh |
| 2010/0234952 A1 | 9/2010 | Peterman |
| 2010/0241231 A1 | 9/2010 | Marino et al. |
| 2010/0249935 A1 | 9/2010 | Slivka et al. |
| 2010/0268345 A1 | 10/2010 | Ralph et al. |
| 2010/0274358 A1 | 10/2010 | Mueller et al. |
| 2010/0280616 A1 | 11/2010 | Frasier |
| 2010/0286777 A1 | 11/2010 | Errico et al. |
| 2010/0286780 A1 | 11/2010 | Dryer et al. |
| 2010/0298942 A1 | 11/2010 | Ransell et al. |
| 2010/0305707 A1 | 12/2010 | Biedermann et al. |
| 2010/0324684 A1 | 12/2010 | Eisermann et al. |
| 2011/0015742 A1 | 1/2011 | Hong |
| 2011/0015747 A1 | 1/2011 | McManus et al. |
| 2011/0046740 A1 | 2/2011 | Chen et al. |

(56) References Cited

U.S. PATENT DOCUMENTS

| | | |
|---|---|---|
| 2011/0046743 A1 | 2/2011 | Perez-Cruet et al. |
| 2011/0077741 A1 | 3/2011 | Heinz |
| 2011/0087294 A1 | 4/2011 | Reiley |
| 2011/0093074 A1 | 4/2011 | Glerum et al. |
| 2011/0137420 A1 | 6/2011 | Michelson |
| 2011/0144753 A1 | 6/2011 | Marchek et al. |
| 2011/0153020 A1 | 6/2011 | Abdelgany et al. |
| 2011/0172775 A1 | 7/2011 | Flickinger et al. |
| 2011/0184518 A1 | 7/2011 | Trieu |
| 2011/0196495 A1 | 8/2011 | Hunt |
| 2011/0202135 A1 | 8/2011 | Baek et al. |
| 2011/0202137 A1 | 8/2011 | Keith et al. |
| 2011/0208312 A1 | 8/2011 | Moskowitz et al. |
| 2011/0208313 A1 | 8/2011 | Michelson |
| 2011/0218633 A1 | 9/2011 | Frey et al. |
| 2011/0230965 A1 | 9/2011 | Schell et al. |
| 2011/0230968 A1 | 9/2011 | Perisic |
| 2011/0251692 A1 | 10/2011 | McLaughlin et al. |
| 2011/0264219 A1 | 10/2011 | Rouben |
| 2011/0282392 A1 | 11/2011 | Murphy et al. |
| 2011/0282453 A1 | 11/2011 | Greenhalgh et al. |
| 2011/0282454 A1 | 11/2011 | Ullrich et al. |
| 2011/0282457 A1 | 11/2011 | Danièle et al. |
| 2011/0295371 A1 | 12/2011 | Moskowitz et al. |
| 2011/0301709 A1 | 12/2011 | Kraus et al. |
| 2011/0301710 A1 | 12/2011 | Mather et al. |
| 2011/0319995 A1 | 12/2011 | Voellmicke et al. |
| 2011/0319999 A1 | 12/2011 | O'Neil et al. |
| 2011/0320000 A1 | 12/2011 | O'Neil et al. |
| 2012/0004730 A1 | 1/2012 | Castro |
| 2012/0035729 A1 | 2/2012 | Glerum et al. |
| 2012/0059470 A1 | 3/2012 | Weiman |
| 2012/0071981 A1 | 3/2012 | Farley et al. |
| 2012/0071983 A1 | 3/2012 | Ray, III et al. |
| 2012/0078373 A1 | 3/2012 | Gamache et al. |
| 2012/0095559 A1 | 4/2012 | Woods et al. |
| 2012/0109305 A1 | 5/2012 | Park |
| 2012/0109319 A1 | 5/2012 | Perisic |
| 2012/0123546 A1 | 5/2012 | Medina |
| 2012/0130496 A1 | 5/2012 | Duffield et al. |
| 2012/0136442 A1 | 5/2012 | Kleiner |
| 2012/0150304 A1 | 6/2012 | Glerum et al. |
| 2012/0150305 A1 | 6/2012 | Glerum et al. |
| 2012/0158143 A1 | 6/2012 | Shapiro |
| 2012/0158145 A1 | 6/2012 | Ralph et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2012/0179260 A1 | 7/2012 | Nottingham |
| 2012/0185047 A1 | 7/2012 | Wooley |
| 2012/0191196 A1 | 7/2012 | Louis et al. |
| 2012/0197401 A1 | 8/2012 | Duncan et al. |
| 2012/0215315 A1 | 8/2012 | Hochschuler et al. |
| 2012/0226356 A1 | 9/2012 | Hirschl |
| 2012/0232660 A1 | 9/2012 | Davenport |
| 2012/0245695 A1 | 9/2012 | Simpson et al. |
| 2012/0265307 A1 | 10/2012 | Guyer et al. |
| 2012/0265311 A1 | 10/2012 | Mather et al. |
| 2012/0271424 A1 | 10/2012 | Crawford |
| 2012/0277866 A1 | 11/2012 | Kalluri et al. |
| 2012/0277868 A1 | 11/2012 | Walters |
| 2012/0277869 A1 | 11/2012 | Siccardi et al. |
| 2012/0277878 A1 | 11/2012 | Sommerich et al. |
| 2012/0290090 A1 | 11/2012 | Glerum |
| 2012/0296433 A1 | 11/2012 | Farin |
| 2012/0310349 A1 | 12/2012 | Gordon et al. |
| 2012/0310356 A1 | 12/2012 | Davis et al. |
| 2012/0323327 A1 | 12/2012 | McAfee |
| 2012/0330419 A1 | 12/2012 | Moskowitz et al. |
| 2012/0330421 A1 | 12/2012 | Weiman |
| 2012/0330426 A1 | 12/2012 | McLaughlin et al. |
| 2013/0006360 A1 | 1/2013 | Aferzon et al. |
| 2013/0006361 A1 | 1/2013 | Glerum et al. |
| 2013/0006365 A1 | 1/2013 | Pepper et al. |
| 2013/0018465 A1 | 1/2013 | Yue |
| 2013/0018468 A1 | 1/2013 | Moskowitz et al. |
| 2013/0018469 A1 | 1/2013 | Moskowitz et al. |
| 2013/0018470 A1 | 1/2013 | Moskowitz et al. |
| 2013/0018471 A1 | 1/2013 | Davenport et al. |
| 2013/0023991 A1 | 1/2013 | Moskowitz et al. |
| 2013/0023992 A1 | 1/2013 | Moskowitz et al. |
| 2013/0053893 A1 | 2/2013 | Gamache et al. |
| 2013/0053894 A1 | 2/2013 | Gamache et al. |
| 2013/0053962 A1 | 2/2013 | Moskowitz et al. |
| 2013/0060339 A1 | 3/2013 | Duffield et al. |
| 2013/0073044 A1 | 3/2013 | Gamache |
| 2013/0085572 A1 | 4/2013 | Glerum et al. |
| 2013/0116791 A1 | 5/2013 | Theofilos |
| 2013/0123923 A1 | 5/2013 | Pavlov et al. |
| 2013/0123924 A1 | 5/2013 | Butler et al. |
| 2013/0123935 A1 | 5/2013 | Hunt et al. |
| 2013/0131812 A1 | 5/2013 | Ganey |
| 2013/0138214 A1 | 5/2013 | Greenhalgh et al. |
| 2013/0150967 A1 | 6/2013 | Shih et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0178904 A1 | 7/2013 | Arcenio et al. |
| 2013/0178940 A1 | 7/2013 | Farley |
| 2013/0184822 A1 | 7/2013 | Kleiner |
| 2013/0184826 A1 | 7/2013 | Thaiyananthan |
| 2013/0190880 A1 | 7/2013 | Schaller |
| 2013/0197642 A1 | 8/2013 | Ernst |
| 2013/0197647 A1 | 8/2013 | Wolters et al. |
| 2013/0204371 A1 | 8/2013 | McLuen et al. |
| 2013/0204373 A1 | 8/2013 | Lambrecht et al. |
| 2013/0204374 A1 | 8/2013 | Milella |
| 2013/0211525 A1 | 8/2013 | McLuen et al. |
| 2013/0218275 A1 | 8/2013 | Caballes |
| 2013/0245763 A1 | 9/2013 | Mauldin |
| 2013/0245765 A1 | 9/2013 | Lowry et al. |
| 2013/0247357 A1 | 9/2013 | Bertele et al. |
| 2013/0253650 A1 | 9/2013 | Ashley et al. |
| 2013/0261748 A1 | 10/2013 | Ashley et al. |
| 2013/0268079 A1 | 10/2013 | Castro |
| 2013/0274883 A1 | 10/2013 | McLuen et al. |
| 2013/0274890 A1 | 10/2013 | McKay |
| 2013/0282126 A1 | 10/2013 | Saidha et al. |
| 2013/0304213 A1 | 11/2013 | Aflatoon et al. |
| 2013/0310940 A1 | 11/2013 | Chauvin et al. |
| 2013/0317615 A1 | 11/2013 | Jimenez et al. |
| 2013/0345813 A1 | 12/2013 | Frank et al. |
| 2013/0345814 A1 | 12/2013 | Walkenhorst et al. |
| 2014/0012383 A1 | 1/2014 | Triplett et al. |
| 2014/0018921 A1 | 1/2014 | Stad et al. |
| 2014/0018922 A1 | 1/2014 | Marino et al. |
| 2014/0018924 A1 | 1/2014 | McManus et al. |
| 2014/0031936 A1 | 1/2014 | Weiman |
| 2014/0031942 A1 | 1/2014 | Ullrich et al. |
| 2014/0039622 A1 | 2/2014 | Glerum et al. |
| 2014/0039627 A1 | 2/2014 | Weiland |
| 2014/0046373 A1 | 2/2014 | Brennan |
| 2014/0046445 A1 | 2/2014 | Brennan |
| 2014/0052252 A1 | 2/2014 | Weiman |
| 2014/0052253 A1 | 2/2014 | Perlott et al. |
| 2014/0052254 A1 | 2/2014 | Glerum et al. |
| 2014/0052258 A1 | 2/2014 | Ball et al. |
| 2014/0052259 A1 | 2/2014 | Garner et al. |
| 2014/0052260 A1 | 2/2014 | McKenny et al. |
| 2014/0058446 A1 | 2/2014 | Bernstein |
| 2014/0058512 A1 | 2/2014 | Petersheim |
| 2014/0058513 A1 | 2/2014 | Gahman et al. |
| 2014/0058514 A1 | 2/2014 | Berry et al. |
| 2014/0058515 A1 | 2/2014 | Hawkins et al. |
| 2014/0058516 A1 | 2/2014 | Glerum et al. |
| 2014/0058518 A1 | 2/2014 | Niemiec et al. |
| 2014/0058519 A1 | 2/2014 | Glerum et al. |
| 2014/0058520 A1 | 2/2014 | Crozet |
| 2014/0058521 A1 | 2/2014 | McLuen et al. |
| 2014/0058522 A1 | 2/2014 | Rhoda |
| 2014/0067071 A1 | 3/2014 | Weiman et al. |
| 2014/0074241 A1 | 3/2014 | McConnell |
| 2014/0088708 A1 | 3/2014 | Mclaughlin et al. |

(56) References Cited

U.S. PATENT DOCUMENTS

| | | |
|---|---|---|
| 2014/0088710 A1 | 3/2014 | Etminan |
| 2014/0088711 A1 | 3/2014 | Chin et al. |
| 2014/0088715 A1 | 3/2014 | Ciupik |
| 2014/0094916 A1 | 4/2014 | Glerum |
| 2014/0094917 A1 | 4/2014 | Salerni |
| 2014/0094918 A1 | 4/2014 | Vishnubholta et al. |
| 2014/0094922 A1 | 4/2014 | Abdou |
| 2014/0100657 A1 | 4/2014 | McCormack et al. |
| 2014/0107785 A1 | 4/2014 | Geisler et al. |
| 2014/0107786 A1 | 4/2014 | Geisler et al. |
| 2014/0114134 A1 | 4/2014 | Theofilos et al. |
| 2014/0114417 A1 | 4/2014 | Theofilos et al. |
| 2014/0114420 A1 | 4/2014 | Robinson |
| 2014/0114421 A1 | 4/2014 | Ullrich et al. |
| 2014/0114422 A1 | 4/2014 | Malandain |
| 2014/0121773 A1 | 5/2014 | Patel et al. |
| 2014/0121774 A1 | 5/2014 | Glerum et al. |
| 2014/0121777 A1 | 5/2014 | Rosen et al. |
| 2014/0128977 A1 | 5/2014 | Glerum et al. |
| 2014/0135930 A1 | 5/2014 | Georges |
| 2014/0135932 A1 | 5/2014 | Davis et al. |
| 2014/0135933 A1 | 5/2014 | McClintock et al. |
| 2014/0142701 A1 | 5/2014 | Weiman |
| 2014/0142704 A1 | 5/2014 | Ralph et al. |
| 2014/0142709 A1 | 5/2014 | Kube, II |
| 2014/0148904 A1 | 5/2014 | Robinson |
| 2014/0156007 A1 | 6/2014 | Pabst et al. |
| 2014/0156008 A1 | 6/2014 | Flickinger et al. |
| 2014/0163686 A1 | 6/2014 | Frasier et al. |
| 2014/0172103 A1 | 6/2014 | O'Neil et al. |
| 2014/0172106 A1 | 6/2014 | To et al. |
| 2014/0180419 A1 | 6/2014 | Dmuschewsky |
| 2014/0188225 A1 | 7/2014 | Dmuschewsky |
| 2014/0188228 A1 | 7/2014 | Thibodeau |
| 2014/0194991 A1 | 7/2014 | Jimenez |
| 2014/0194992 A1 | 7/2014 | Medina |
| 2014/0200669 A1 | 7/2014 | Berger et al. |
| 2014/0207235 A1 | 7/2014 | Drapeau |
| 2014/0207238 A1 | 7/2014 | Theofilis et al. |
| 2014/0222151 A1 | 8/2014 | Refai et al. |
| 2014/0228955 A1 | 8/2014 | Weiman |
| 2014/0236296 A1 | 8/2014 | Wagner et al. |
| 2014/0236297 A1 | 8/2014 | Iott et al. |
| 2014/0236298 A1 | 8/2014 | Pinto |
| 2014/0243983 A1 | 8/2014 | Galea et al. |
| 2014/0249589 A1 | 9/2014 | Reiley et al. |
| 2014/0249628 A1 | 9/2014 | Weiman |
| 2014/0249629 A1 | 9/2014 | Moskowitz et al. |
| 2014/0257484 A1 | 9/2014 | Flower et al. |
| 2014/0257485 A1 | 9/2014 | Matthis et al. |
| 2014/0257486 A1 | 9/2014 | Alheidt |
| 2014/0277139 A1 | 9/2014 | Vrionis et al. |
| 2014/0277464 A1 | 9/2014 | Richter et al. |
| 2014/0277471 A1 | 9/2014 | Gray et al. |
| 2014/0277472 A1 | 9/2014 | Gray et al. |
| 2014/0277473 A1 | 9/2014 | Perrow |
| 2014/0277474 A1 | 9/2014 | Robinson et al. |
| 2014/0277475 A1 | 9/2014 | De Villiers et al. |
| 2014/0277484 A1 | 9/2014 | Prevost et al. |
| 2014/0277497 A1 | 9/2014 | Bennett et al. |
| 2014/0277498 A1 | 9/2014 | Ainsworth et al. |
| 2014/0277499 A1 | 9/2014 | Ainsworth et al. |
| 2014/0277508 A1 | 9/2014 | Baynham |
| 2014/0288652 A1 | 9/2014 | Boehm et al. |
| 2014/0296982 A1 | 10/2014 | Cheng |
| 2014/0296983 A1 | 10/2014 | Fauth et al. |
| 2014/0296984 A1 | 10/2014 | Etminan |
| 2014/0303731 A1 | 10/2014 | Glerum |

FOREIGN PATENT DOCUMENTS

| | | | |
|---|---|---|---|
| EP | 646366 | B1 | 12/1997 |
| EP | 834295 | A1 | 4/1998 |
| EP | 369603 | B1 | 5/1998 |
| EP | 498816 | B1 | 11/1998 |
| EP | 966929 | A2 | 12/1999 |
| EP | 760639 | B1 | 4/2000 |
| EP | 1043002 | A2 | 10/2000 |
| EP | 1082950 | A1 | 3/2001 |
| EP | 857041 | B1 | 4/2001 |
| EP | 1099429 | A1 | 5/2001 |
| EP | 844856 | B1 | 10/2001 |
| EP | 1138285 | A1 | 10/2001 |
| EP | 871419 | B1 | 11/2001 |
| EP | 720455 | B1 | 1/2002 |
| EP | 734703 | B1 | 2/2002 |
| EP | 781113 | B1 | 3/2002 |
| EP | 716840 | B1 | 5/2002 |
| EP | 784967 | B1 | 11/2002 |
| EP | 1175878 | B1 | 3/2003 |
| EP | 1147751 | B1 | 5/2003 |
| EP | 1328217 | A2 | 7/2003 |
| EP | 855887 | B1 | 8/2003 |
| EP | 1006955 | B1 | 8/2003 |
| EP | 977526 | B1 | 9/2003 |
| EP | 831759 | B1 | 3/2004 |
| EP | 1014899 | B1 | 8/2004 |
| EP | 1033941 | B1 | 8/2004 |
| EP | 1132061 | B1 | 8/2004 |
| EP | 1063949 | B1 | 9/2004 |
| EP | 1011481 | B1 | 10/2004 |
| EP | 1051133 | B1 | 10/2004 |
| EP | 1107711 | B1 | 10/2004 |
| EP | 1272130 | B1 | 11/2004 |
| EP | 888099 | B1 | 1/2005 |
| EP | 1278486 | B1 | 3/2005 |
| EP | 836454 | B1 | 4/2005 |
| EP | 1255516 | B1 | 4/2005 |
| EP | 1364617 | B1 | 8/2005 |
| EP | 1124511 | B1 | 9/2005 |
| EP | 1139930 | B1 | 9/2005 |
| EP | 1350489 | B1 | 10/2005 |
| EP | 853932 | B1 | 11/2005 |
| EP | 1076536 | B1 | 11/2005 |
| EP | 891169 | B1 | 12/2005 |
| EP | 1164979 | B1 | 12/2005 |
| EP | 1233732 | B1 | 5/2006 |
| EP | 1280481 | B1 | 7/2006 |
| EP | 1189557 | B1 | 8/2006 |
| EP | 1211985 | B1 | 9/2006 |
| EP | 1009338 | B1 | 10/2006 |
| EP | 1481654 | B1 | 10/2006 |
| EP | 1351610 | B1 | 12/2006 |
| EP | 1374806 | B1 | 12/2006 |
| EP | 1138267 | B1 | 3/2007 |
| EP | 1504732 | B1 | 5/2007 |
| EP | 1009337 | B1 | 6/2007 |
| EP | 1023010 | B1 | 6/2007 |
| EP | 1284689 | B1 | 6/2007 |
| EP | 1532949 | B1 | 7/2007 |
| EP | 1464307 | B1 | 8/2007 |
| EP | 1585466 | B1 | 8/2007 |
| EP | 1698305 | B1 | 8/2007 |
| EP | 1148849 | B1 | 12/2007 |
| EP | 1523963 | B1 | 12/2007 |
| EP | 1554995 | B1 | 12/2007 |
| EP | 1504735 | B1 | 1/2008 |
| EP | 1123069 | B1 | 2/2008 |
| EP | 1330188 | B1 | 2/2008 |
| EP | 1290985 | B1 | 4/2008 |
| EP | 1391189 | B1 | 6/2008 |
| EP | 1567096 | B1 | 7/2008 |
| EP | 1194087 | B1 | 8/2008 |
| EP | 1437105 | B1 | 10/2008 |
| EP | 1139936 | B1 | 12/2008 |
| EP | 1389978 | B1 | 1/2009 |
| EP | 1011503 | B1 | 4/2009 |
| EP | 1341491 | B1 | 4/2009 |
| EP | 1469800 | B1 | 4/2009 |
| EP | 1925271 | B1 | 8/2009 |
| EP | 1506753 | B1 | 9/2009 |
| EP | 1554994 | B1 | 9/2009 |
| EP | 1645248 | B1 | 9/2009 |

(56) References Cited

FOREIGN PATENT DOCUMENTS

| | | |
|---|---|---|
| EP | 1829503 B1 | 9/2009 |
| EP | 1011545 B1 | 12/2009 |
| EP | 1841385 B1 | 3/2010 |
| EP | 1843723 B1 | 3/2010 |
| EP | 1408889 B1 | 6/2010 |
| EP | 1774926 B1 | 6/2010 |
| EP | 2111823 B1 | 8/2010 |
| EP | 1706075 B1 | 1/2011 |
| EP | 1762202 B1 | 1/2011 |
| EP | 1301149 B1 | 2/2011 |
| EP | 1903994 B1 | 2/2011 |
| EP | 1372541 B1 | 3/2011 |
| EP | 1321115 B1 | 7/2011 |
| EP | 1400221 B1 | 9/2011 |
| EP | 2108340 B1 | 9/2011 |
| EP | 2368528 A1 | 9/2011 |
| EP | 1385457 B1 | 10/2011 |
| EP | 1732480 B1 | 2/2012 |
| EP | 2157938 B1 | 2/2012 |
| EP | 2327377 B1 | 3/2012 |
| EP | 1478309 B1 | 4/2012 |
| EP | 1699389 B1 | 4/2012 |
| EP | 2018827 B1 | 5/2012 |
| EP | 2234564 B1 | 5/2012 |
| EP | 2237748 B1 | 9/2012 |
| EP | 2194929 B1 | 10/2012 |
| EP | 1430858 B1 | 11/2012 |
| EP | 1463465 B1 | 11/2012 |
| EP | 2340776 B1 | 1/2013 |
| EP | 1838248 B1 | 3/2013 |
| EP | 2055267 B1 | 4/2013 |
| EP | 2361572 B1 | 4/2013 |
| EP | 1198208 B1 | 7/2013 |
| EP | 2632391 A1 | 9/2013 |
| EP | 2249747 B1 | 12/2013 |
| EP | 2083760 B1 | 1/2014 |
| EP | 2677971 A2 | 1/2014 |
| EP | 2065016 B1 | 4/2014 |
| EP | 2376026 B1 | 4/2014 |
| EP | 2729091 A1 | 5/2014 |
| EP | 2142147 B1 | 7/2014 |
| EP | 2207504 B1 | 7/2014 |
| EP | 2376030 B1 | 8/2014 |
| EP | 2760376 A1 | 8/2014 |
| EP | 2764851 A1 | 8/2014 |
| EP | 2777633 A2 | 9/2014 |
| EP | 2779953 A2 | 9/2014 |
| FR | 2 841 124 | 12/2003 |
| WO | WO9614809 A1 | 5/1996 |
| WO | WO9622747 A1 | 8/1996 |
| WO | WO9723174 A1 | 7/1997 |
| WO | WO 97/32547 | 9/1997 |
| WO | WO 97/37619 | 10/1997 |
| WO | WO9842269 A1 | 10/1998 |
| WO | WO0209597 A2 | 2/2002 |
| WO | WO04000176 A1 | 12/2003 |
| WO | WO2006134262 A1 | 12/2006 |
| WO | WO2008044057 A1 | 4/2008 |
| WO | WO2008112607 A2 | 9/2008 |
| WO | WO2008152499 A2 | 12/2008 |
| WO | WO2009040840 A1 | 4/2009 |
| WO | WO2009064787 A2 | 5/2009 |
| WO | WO2009091775 A2 | 7/2009 |
| WO | WO2010148112 A1 | 12/2010 |
| WO | WO2011056172 A1 | 5/2011 |
| WO | WO2011116136 | 9/2011 |
| WO | WO2011142761 A1 | 11/2011 |
| WO | WO2012056119 A1 | 5/2012 |
| WO | WO2012117312 A2 | 9/2012 |
| WO | WO2013007888 A1 | 1/2013 |
| WO | WO2013008111 A1 | 1/2013 |
| WO | WO2013048000 A2 | 4/2013 |
| WO | WO2013142480 A1 | 9/2013 |
| WO | WO2013158294 A1 | 10/2013 |
| WO | WO2013175147 A1 | 11/2013 |
| WO | WO2013184946 A1 | 12/2013 |
| WO | WO2014035835 A1 | 3/2014 |
| WO | WO2014063255 A1 | 5/2014 |
| WO | WO2014118291 A1 | 8/2014 |
| WO | WO2014144696 A1 | 9/2014 |
| WO | WO2014158619 A1 | 10/2014 |
| WO | WO2014159739 A1 | 10/2014 |
| WO | WO2014159762 A1 | 10/2014 |

OTHER PUBLICATIONS

Butterman et al., *Interbody device endplate engagement effects on motion segment biomechanics*, The Spine Journal, 9(7):pp. 564-573, Jul. 2009.

Product information in 1 page for an implant named *Cross-Fuse® Lateral Option System* by Pioneer Surgical Technology, Inc. (dated 2011 and retrieved on or about Aug. 2012 from www.pioneersurgical.com/international/index.php?option=com_content&view=article&id=72&Itemid=72).

Product information in 1 page for an implant named *TransContinental® Spacer System* by Globus Medical, Inc. (retrieved on or about Aug. 2012 from www.globusmedical.com/intervertebral-fusion/220-transcontinental).

Product information in 1 page for an implant named *CoRoent® Interbody/VBR Implant* by NuVasive, Inc. (retrieved on or about Aug. 2012 as a partial image (screenshot) capture from www.nuvasive.com/health-providers/innovative-solutions/).

Wright, N.M., MD, *Biomechanical Testing of XLIF Constructs-Stand-Alone Interbody Versus Interbody Supplemented with Lateral or Posterior Instrumentation*, Digital Poster presented at the Congress of Neurological Surgeons (CNS) Annual Conference 2005 in Boston, Massachusetts (Oct. 8, 2005-Oct. 13, 2005), which illustrates and discusses, inter alia, an implant named *CoRoent* by NuVasive, Inc.

DeWald, R.L., "Spinal Deformities: The Comprehensive Text," (*partial excerpt from book*), published Mar. 15, 2003.

* cited by examiner

US 9,380,932 B1

RETRACTOR DEVICES FOR MINIMALLY INVASIVE ACCESS TO THE SPINE

PRIORITY DATA

This application claims the priority benefit under 35 U.S.C. §119(e) of U.S. Provisional Application No. 61/554,958, filed Nov. 2, 2011, the entirety of which is hereby incorporated by reference herein.

BACKGROUND

1. Field

This application generally relates to spinal treatment, and more specifically, to devices and instrumentation for accessing certain portions of the spine minimally invasively, and related systems and methods.

2. Description of the Related Art

Intervertebral discs can degenerate or otherwise become damaged over time. In some instances, an intervertebral implant can be positioned within a space previously occupied by a disc. Such implants can help maintain a desired spacing between adjacent vertebrae and/or promote fusion between adjacent vertebrae. In order to minimally invasively access a target portion of the spine, retractors and/or other access devices can be used. Accordingly, a need exists for improved retractor devices, as well as related instrumentation, tools, systems and methods.

SUMMARY

According to some embodiments, a retractor device for selectively moving (e.g., retracting) anatomical tissue of a subject during a minimally invasive procedure (e.g., accessing the lumbar or other portion of a spine during a spinal fusion procedure) comprises a main body comprising at least three sides (e.g., three, four, five sides, more than five sides, etc.). In some embodiments, the main body defines or otherwise forms a central opening, which comprises a center-point positioned along a centerline of the central opening. In some embodiments, the retractor device further comprises a plurality of movable members secured to the main body.

According to some embodiments, each side of the retractor device comprises a movable member. In other embodiments, the main body comprises a generally circular, oval or non-polygonal shape. In such embodiments, a plurality of movable members (e.g., two, three, four, more than four, etc.) is secured to the circular, oval or non-polygonal main body. According to some embodiments, a blade is secured to each movable member and configured to be moved together with a corresponding movable member to which the blade is secured. In some embodiments, each blade extends generally perpendicular to the main body.

In some embodiments, the blade comprises a distal end configured to extend into an anatomy of the subject. In some embodiments, each movable member is configured to move laterally relative to the main body, such that the blades secured to the movable members can be moved within the central opening defined by the main body. In some embodiments, each of the blades is configured to be selectively moved laterally past the center-point of the central opening. In one embodiment, each of the blades is configured to be selectively rotated (e.g., toe in or tow out) relative to an axis generally perpendicular to the main body. In some embodiments, the movable members are configured to be moved relative to one another so that the blades attached to said movable members generally form a cylindrical opening within the central opening defined by the main body.

According to some embodiments, the main body comprises four or more sides. In some embodiments, the main body comprises one or more of the following shapes: square, other rectangular, pentagonal, triangular, hexagonal, other polygonal, circular, oval, irregular and the like. In some embodiments, each of the blades is removably secured to a corresponding movable member. In some embodiments, at least of the blades is irremovably secured to a corresponding movable member. In some embodiments, each movable member is operatively coupled to a first controller and a second controller, wherein the first controller is configured to selectively adjust a lateral position of the movable member (e.g., to move the movable member and a blade secured thereto closer or further away from an adjacent movable member and blade). In some embodiments, the second controller is configured to selectively rotate the blade attached to the movable member (e.g., toe-in or toe-out). In some embodiments, each of the movable members and the corresponding blade secured thereto can be moved independently of one or more of the other movable members and corresponding blades.

According to some embodiments, the first controller and/or the second controller comprises a rotatable knob, a button, a lever, a release mechanism and/or the like. In one embodiment, the movable members are moved using a rack and pinion mechanism, another gear and/or mechanical system. In some embodiments, the blade comprises at least one slot, channel, recess or other receiving portion. In some embodiments, such a slot extends along at least a portion of the length of the blade (e.g., only along a portion of the blade length, along the entire or substantially along the entire blade length, etc.). In some embodiments, at least one slot of the blade is configured to slidably receive a shim, said shim being configured to generally extend a distal end of said blade (e.g., to extend the length of the blade so as to reach a nerve or other sensitive anatomical area that can be selectively moved by the shim and blade). In some embodiments, the blade is configured to slidably receive an illumination device configured to provide light to a portion of the subject's anatomy being accessed. In some embodiments, the illumination device comprises a fiber-optic, LED and/or other light source.

BRIEF DESCRIPTION OF THE DRAWINGS

These and other features, aspects and advantages of the present application are described with reference to drawings of certain embodiments, which are intended to illustrate, but not to limit, the present disclosure. It is to be understood that these drawings are for the purpose of illustrating concepts of the present disclosure and may not be to scale.

DETAILED DESCRIPTION

A variety of embodiments and examples described herein illustrate various configurations that may be employed to achieve desired improvements. The particular embodiments and examples are only illustrative and not intended in any way to restrict the general nature of the inventions presented and the various aspects and features of and relating to these inventions.

FIGS. 1 through 13 illustrate various perspective views of one embodiment of a retractor 2000 that is particularly useful in procedures using a lateral access approach to a targeted portion of the spine. As shown, the overall shape of the retractor 2000 can be generally rectangular (e.g., square) or diamond. However, in other embodiments, the shape of the retractor can vary, as desired or required. For instance, in some embodiments, the retractor comprises a generally circular, oval, other polygonal (e.g., triangular, pentagonal, hexagonal, octagonal, etc.), irregular and/or any other shape. The retractor can be used in a variety of minimally invasive approaches to a subject's spine, including without limitation, lateral, posterior, transforaminal and/or any other approach, as desired or required. In addition, the retractor can be used to access any portion of a subject's spine, including the lumbar portion, thoracic portion, cervical portion and/or the like.

Figure 1:
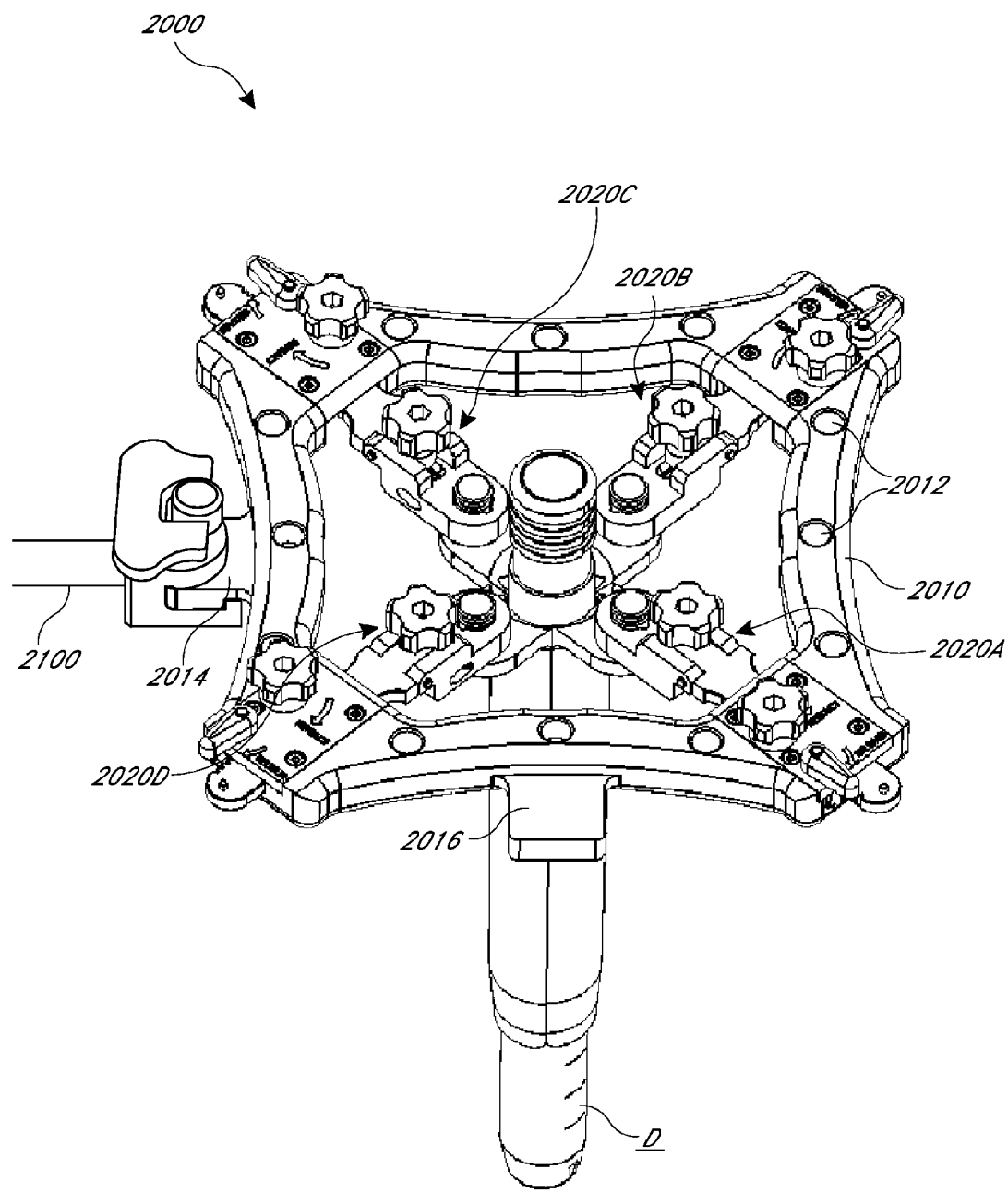
FIGS. 1-13 illustrate various perspective views of one embodiment of a retractor used to access a targeted portion of a patient's spine.
Figure 2:
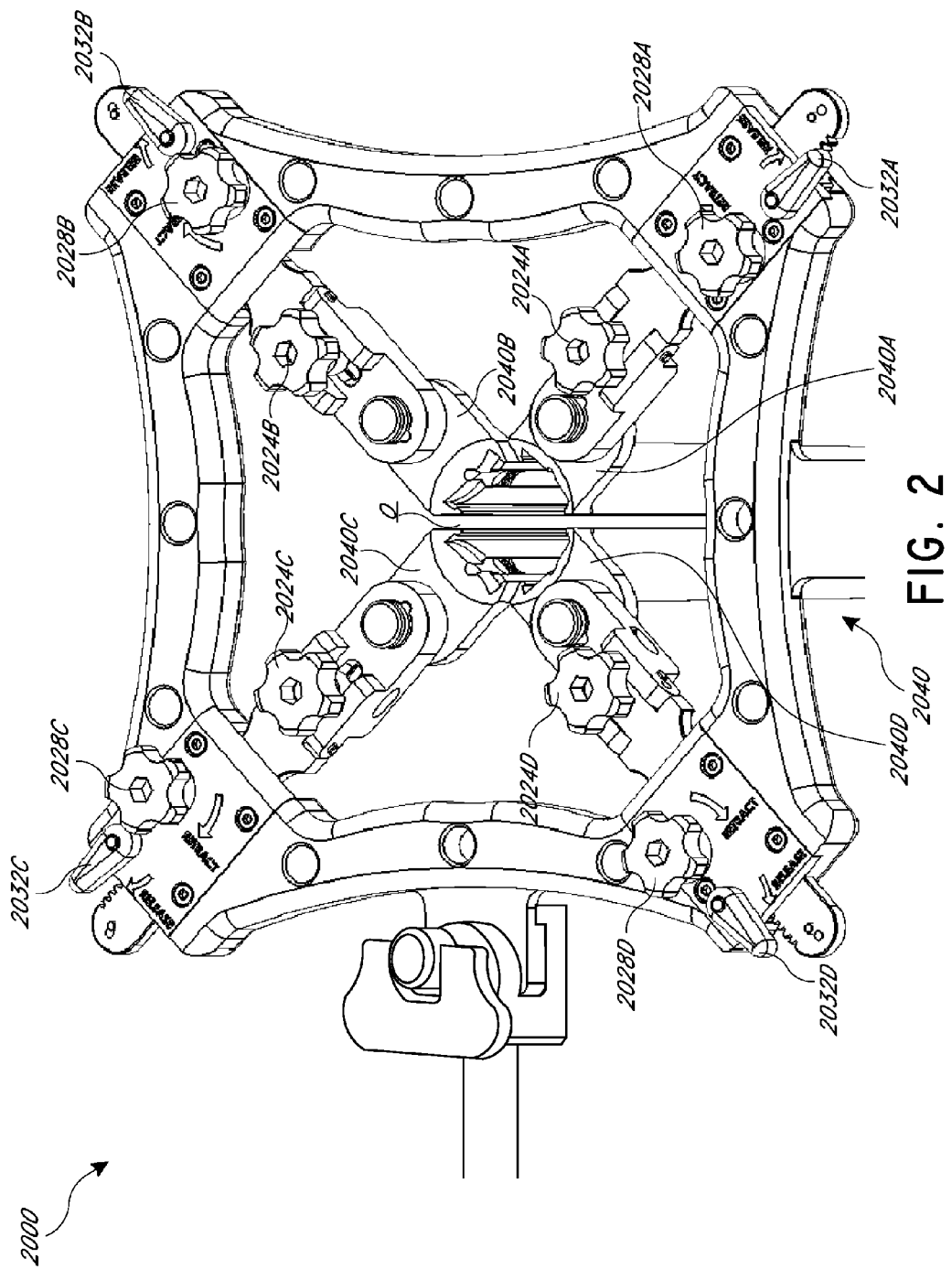

With continued reference to FIG. 1, the retractor 2000 can include one or more sites 2014, 2016 to which a rigid arm 2100 may attach. In some embodiments, the arm 2100 is coupled to a surgery table and/or other fixed or immovable object in order to properly secure the retractor during a particular procedure. In the illustrated embodiment, the retractor comprises a total of four movable members 2020A-2020D that are generally offset by about 90 degrees relative to each other. As is discussed in greater detail herein, the movable members 2020A-2020D can be configured to be selectively moved either toward or away from one another during the course of a particular surgery, as desired or required. In some embodiments, the movable members 2020A-2020D can be moved independently of one another. This can help improve the retractor's flexibility and can facilitate the manner in which tissue is retracted by the surgeon. In one embodiment, each movable member 2020A-2020D is adapted to securely receive a blade 2040.

In some embodiments, the retractor comprises more or fewer than four movable members 2020A-2020D (e.g., two, three, five, six, more than six, etc.), as desired or required for a particular application or procedure. Accordingly, a retractor can include more or fewer than four blades 2040. In some embodiments, the blades are configured to generally form a cylinder when moved adjacent to one another. As discussed in greater detail herein (e.g., with reference to FIGS. 17 and 18), an alignment device can be used to ensure than the blades are properly aligned relative to one another and/or with one or more tissue dilators used in a procedure.

With continued reference to the embodiment illustrated in FIGS. 1-14, each of the blades 2040 generally extends about a quarter of a circle (e.g., approximately 90 degrees). Therefore, when the blades 2040 are moved toward the center-point CP (FIG. 14) of the retractor 2000, the blades cooperate to form a generally full cylindrical shape. Thus, the blades can be generally identical to one another. However, in other arrangements, one or more of the blades can be disproportionally larger than one or more of the other blades. Further, in retractor comprising more or fewer than four blades 2040, the circumferential or radial extent of each blade can be less or more than about 90 degrees. For example, in embodiments comprising three blades and five blades, each blade can extend approximately 120 degrees and 72 degrees, respectively.

As best illustrated in FIG. 1, the blades 2040 can be configured to converge or otherwise come in proximity with one another (e.g., toward the center-point CP of the retractor 2000) so as to snugly surround a dilator D (e.g., a dilator with a diameter of about 18 mm). For example, the retractor can be inserted within a patient's anatomy when the blades are in the orientation depicted in FIG. 1 by sliding the blades 2040 along the outer surface of a dilator. In some embodiments, once the blades have been advanced into the patient's anatomy, the dilator D can be removed. In one embodiment, in addition to having a desired lateral orientation relative to one another so as to help form a generally cylindrical shape, the blades 2040 can be tilted, angled or otherwise skewed (e.g., toe-in, toe-out, etc.) relative to the outer surface of a dilator D. For example, the blades can be oriented so that their distal ends are tilted slightly (e.g., between about 0 and 10 degrees) toward the center-point CP of the retractor 2000. This can help ensure that the blades remain against or along the outer surface of a dilator D as the retractor is advanced into a patient's anatomy. In some embodiments, such a "hugging" feature can help prevent or reduce the likelihood of blade splaying.

With continued reference to FIGS. 1-14, each movable member 2020A-2020D of the retractor 2000 can comprise one or more dials or other controllers. For example, in the illustrated arrangement, each movable member 2020A-2020D comprises an inner dial 2024A-2024D and an outer dial 2028A-2028D. Each dial or other controller or feature can be advantageously used to change the position, orientation and/or other positional aspect of the corresponding blade 2040. In some embodiments, for example, the outer dials 2028A-2028D change the lateral position of the movable members. Thus, the outer dials 2028A-2028D permit a surgeon or other practitioner to adjust the position of the movable members (and thus the blades 2040 connected thereto) relative to one another (e.g., generally along the plane in which the movable members 2020A-2020D are located). By way of example, rotating the outer dial or knob 2024 (e.g., in a clockwise direction) causes the corresponding movable member 2020A-2020D (and thus, the blade attached thereto) to retract or move away from the center-point CP of the retractor. In other embodiments, however, controllers can be of a different type (e.g., other types of knobs, dials, levers, buttons, etc.) and/or controller can operate differently, as desired or required by a particular application or use.

According to some embodiments, the movable members 2020A-2020D comprise rack and pinion systems. Thus, each outer dial or knob 2028A-2028D can be mechanically coupled to a corresponding rack and pinion in order to retract the blade 2040. Further, each movable member 2020A-2020D can comprise a release 2032A-2032D, which causes the rack and pinion to temporarily disengage. Such a release allows one or more of the blades to be quickly moved to a desired lateral position. Thus, the movable members 2020A-2020D (together with the corresponding blades 2040A-2040D) can be moved toward their original position (e.g., to or near the center-point CP of the retractor 2000).

In some embodiments, the inner dials or knobs 2024A-2024D are configured to modify the pitch or angle of the corresponding blades 2040A-2040D. Thus, by rotating such a dial 2024A-2024D (e.g., in a clockwise direction), the distal free end of the corresponding blade 2040A-2040D can tilt or otherwise move relative to the proximal end (e.g., the end that is coupled to the movable member). In some embodiments, the inner dial or knob can be rotated in both directions in order to permit the distal end of the blade to be moved either away or toward the center-point CP of the retractor. In some embodiments, each blade, due in part to the ability to adjust in toe-in or toe-out orientation (e.g., using the inner dials), can be independently moved past the center-point CP (e.g., or a longitudinal axis extending through the center-point CP) of the retractor. Such a configuration can advantageously enhance the surgeon's ability to easily and robustly customize the position of the blades within a patient's anatomy. For example, one or more of the blades can include a toe-out orientation (e.g., tilted toward the center-point CP), while other blades can include a toe-in orientation (e.g., tilted away from the center-point CP). In addition, the distal end of one or more of the blades 2040 can be moved past the center-point CP, as desired or required. The ability of the blades to move past the CP of the retractor can advantageously eliminate the needs for extra instrumentation (e.g., a separate device that would otherwise be inserted within the central opening of the retractor to selectively move tissue) and/or eliminate the need for additional personnel required to perform a particular procedure.

In some embodiments, moving a movable member using the inner dial (e.g., generally along the same plane of the movable members) is referred to dragging the blade. Further, moving the distal or free end of the blade using the outer dial can be referred to as sweeping the blade. Thus, in some embodiments, the retractors disclosed herein, or equivalents thereof, are capable of dragging and/or sweeping each blade independently of one another. In addition, the retractor can be advantageously configured so that each blade can be independently swept past the center-point CP of the retractor (e.g., or the longitudinal axis positioned along the center-point CP). According to some embodiments, the blades maintain a particular tilt or angle once the inner dials have been adjusted, without the need to maintain resistance or other opposing force.

Figure 3:
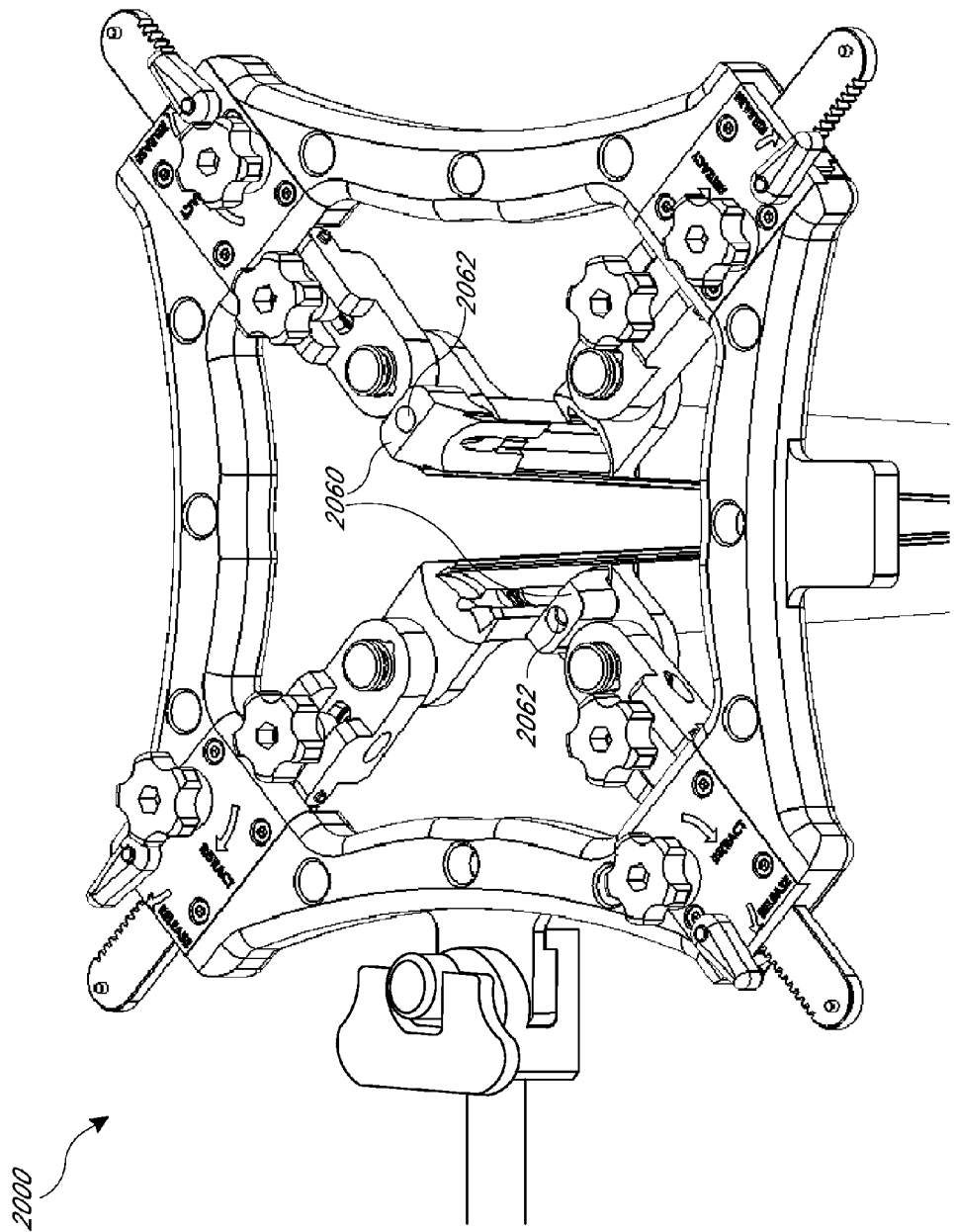
Figure 4:
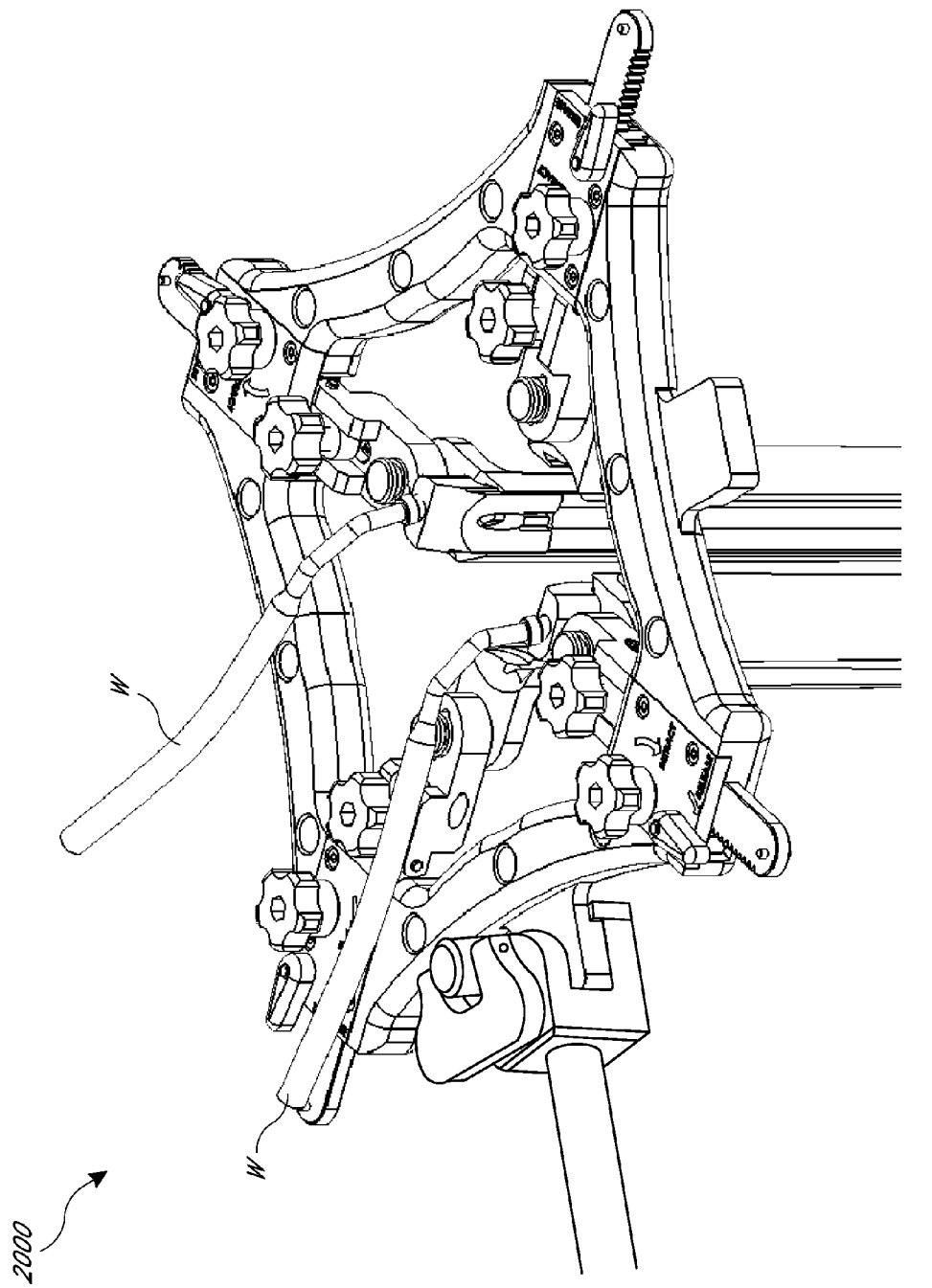
Figure 5:
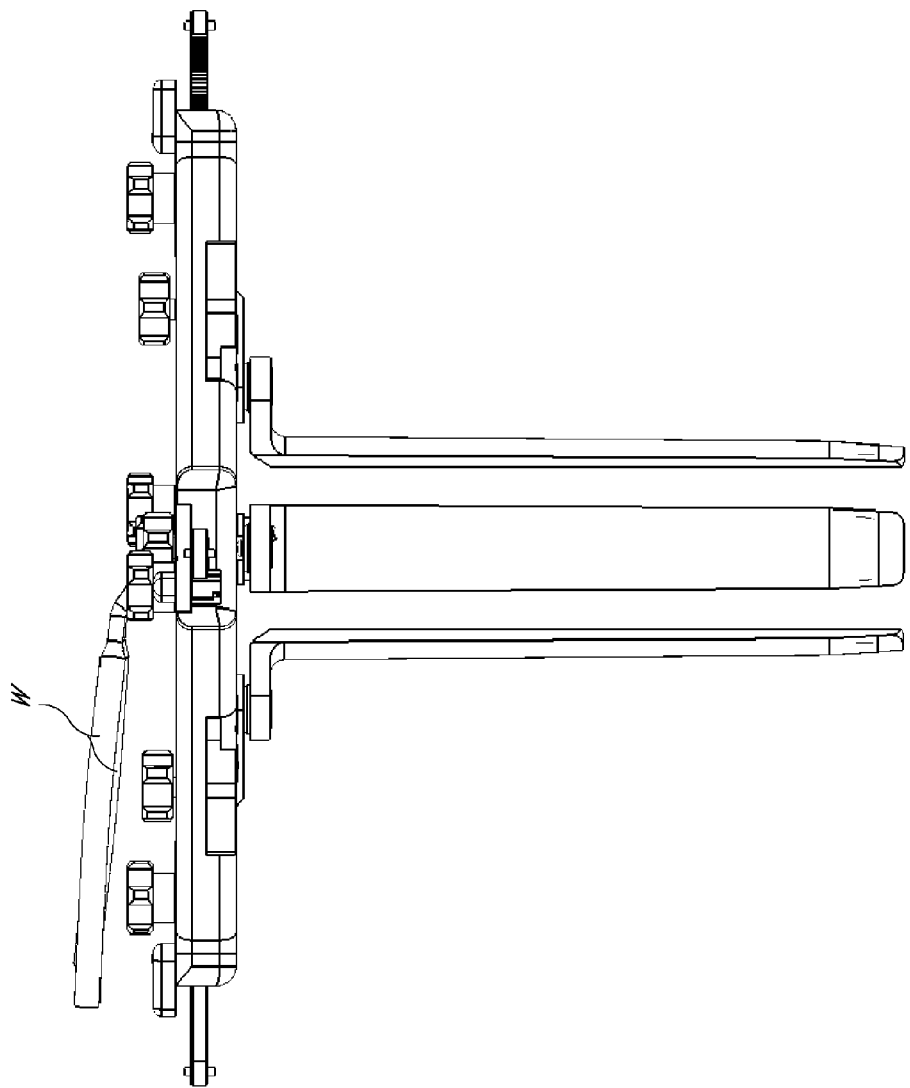
Figure 6:
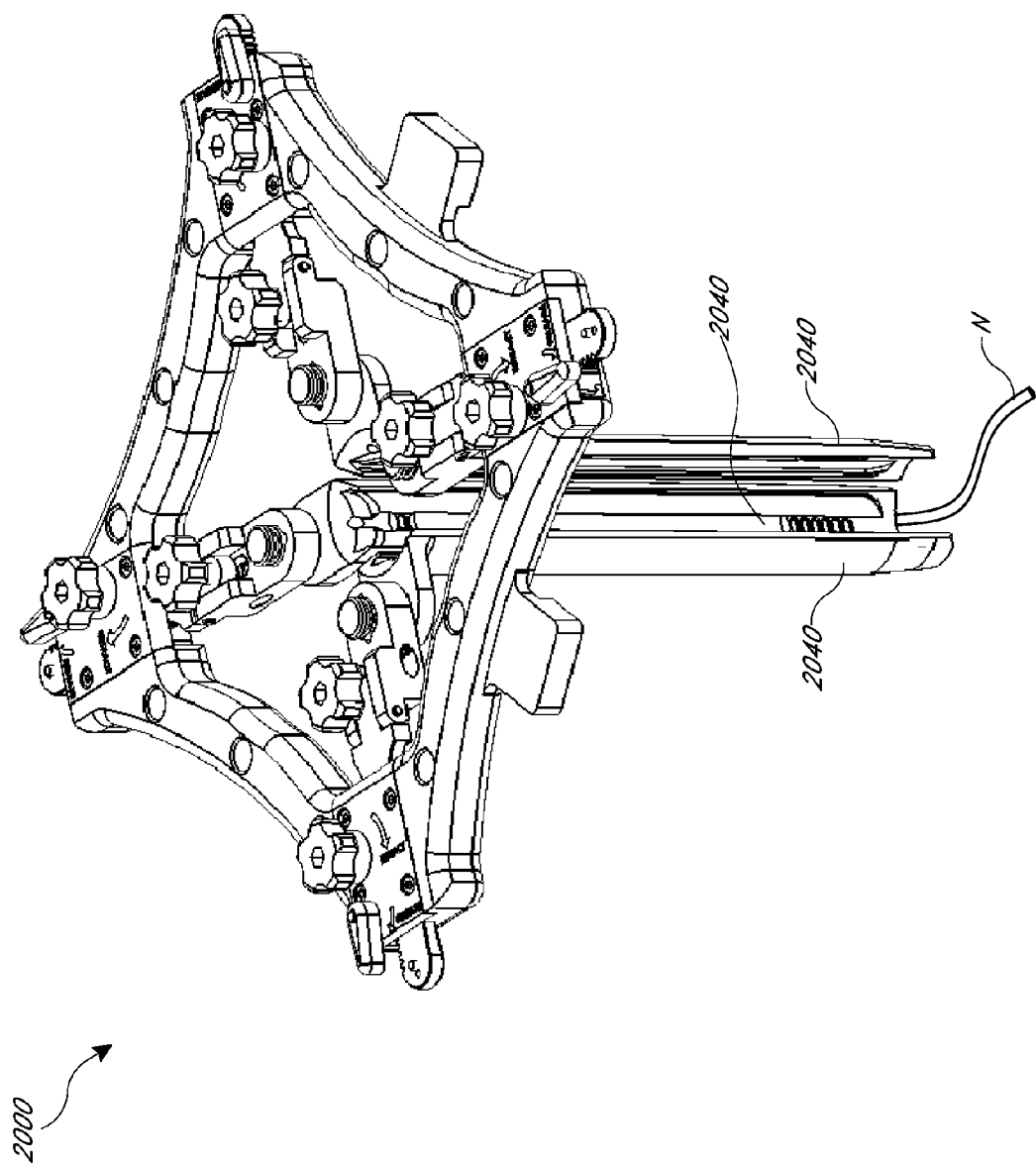
Figure 7:
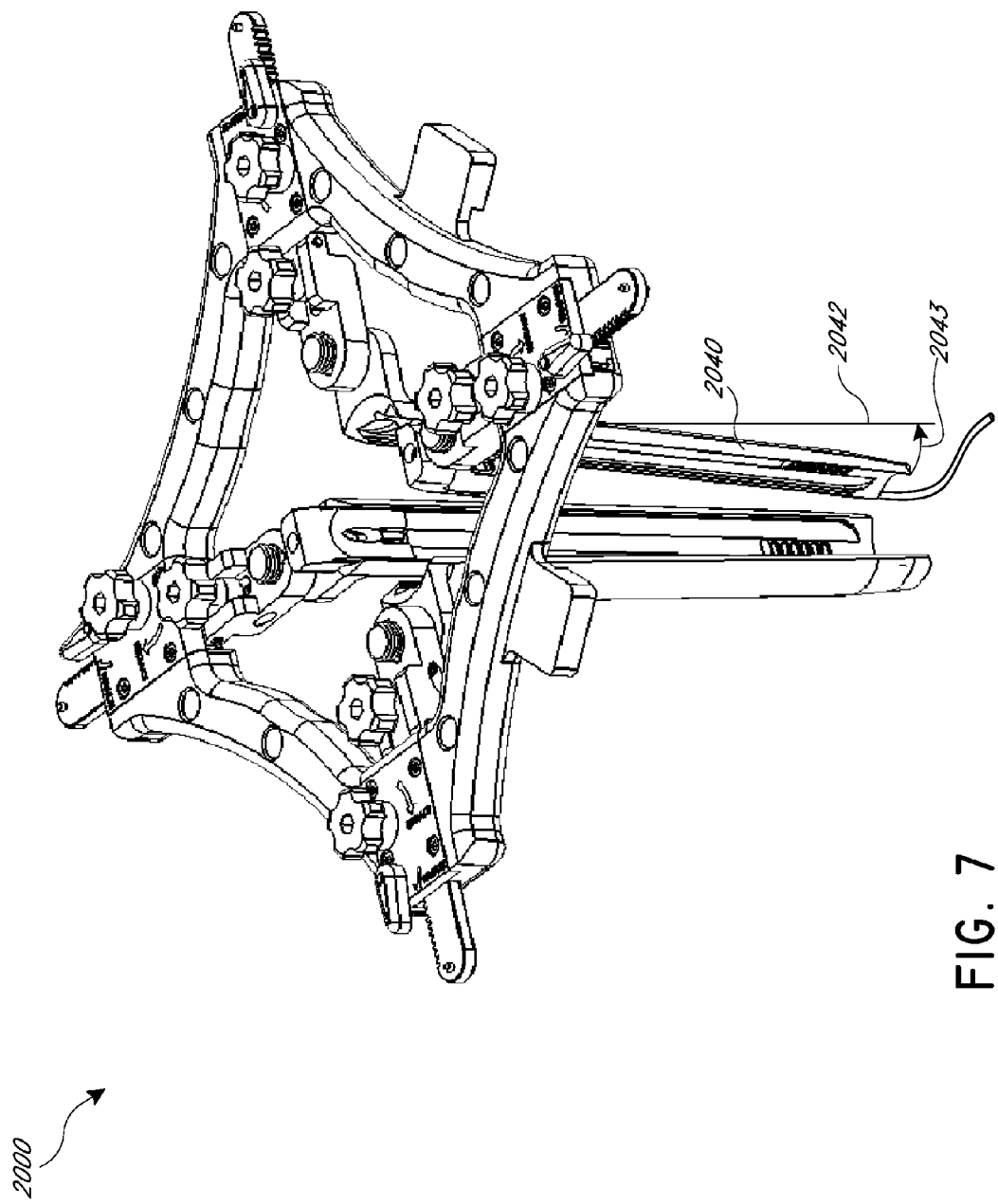

In FIG. 3, the retractor 2000 comprises light shims or coupling members 2060 that are secured along the top portions of two of the blades 2040. Such light shims or coupling members 2060 can be sized, shaped and otherwise configured to releasably or permanently couple to a corresponding portion of the movable member and/or blade. In some embodiments, a light shim 2060 comprises one or more openings 2062 through which a wire W (e.g., a Kirschner Wire or K Wire) can pass.

Figure 18:
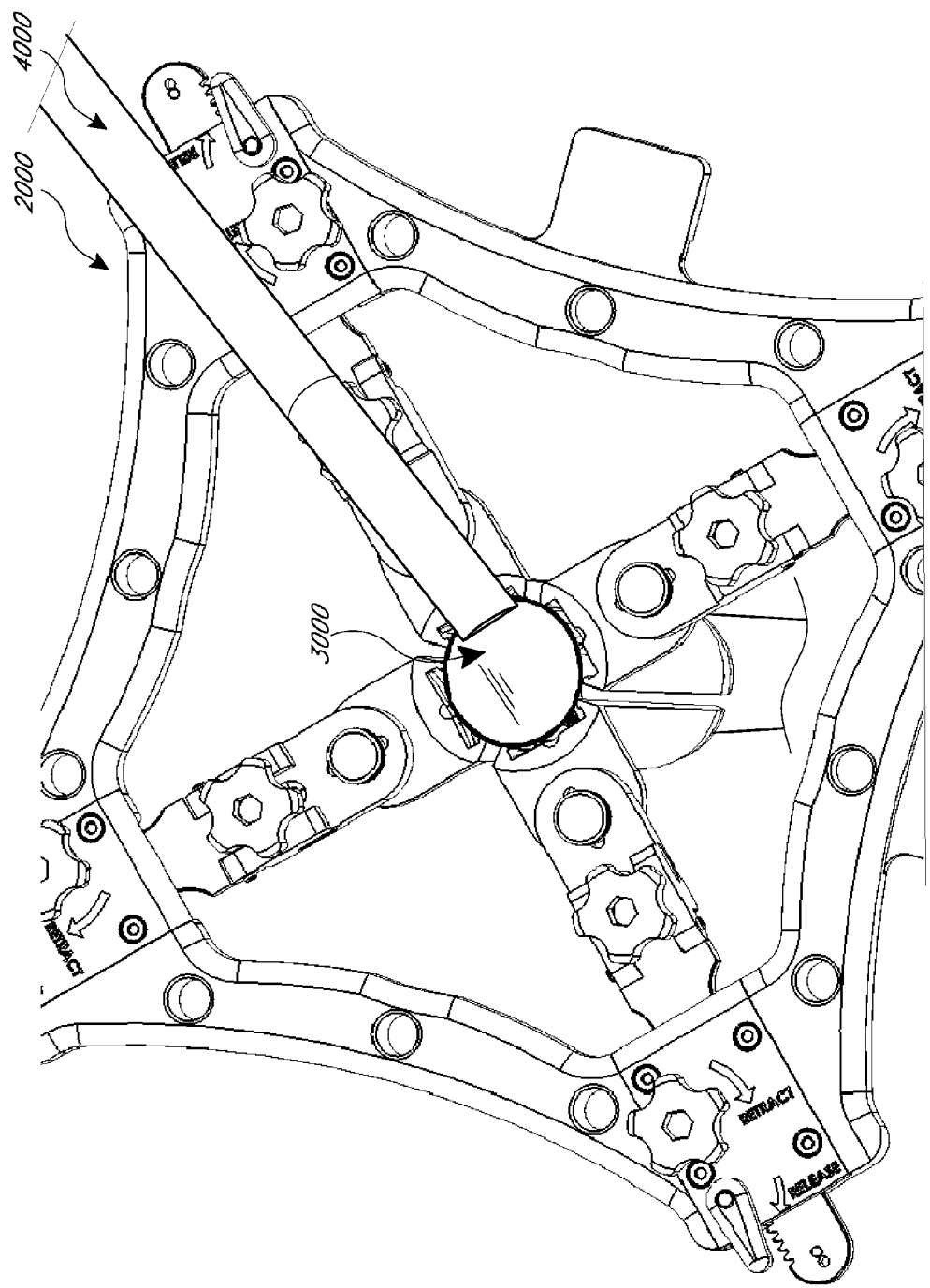
FIG. 18 illustrates a perspective view of the retractor device of FIG. 17 being used together with one embodiment of a retractor in order to generally align the blades secured to said retractor.
Figure 19:
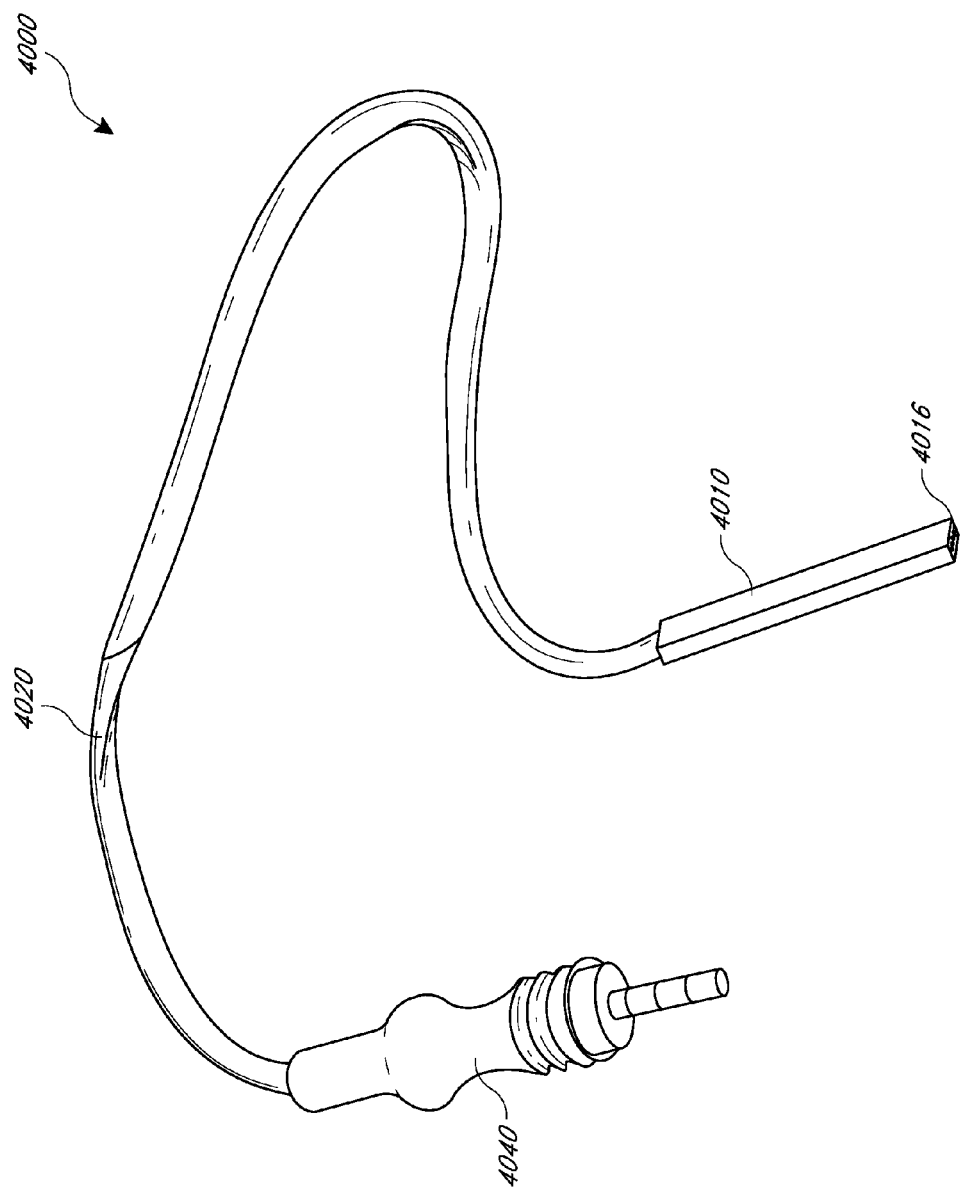
FIG. 19 illustrates one embodiment of the illumination device or component secured to the retractor of FIG. 18.

However, in other embodiments, a light source or illumination device can be configured to releasably secure to one or more blades or other portions of the retractor. For example, as illustrated in FIGS. 18 and 19 and discussed in greater detail below, a fiber-optic light device can be sized and shaped to slide at least partially within a slot or other opening of a blade.

As discussed above and illustrated in FIG. 7, the distal end of the blade 2040 can be configured to be selectively tilted (e.g. either in a toe-in or toe-out orientation) along a particular angle range 2042. For example, the blade 2040 can be tilted or angled using one or more dials or knobs. Such a feature can facilitate moving one or more of the blades 2040 of the retractor 2000 around and past a nerve bundle N or other portion of the anatomy.

Figure 8:
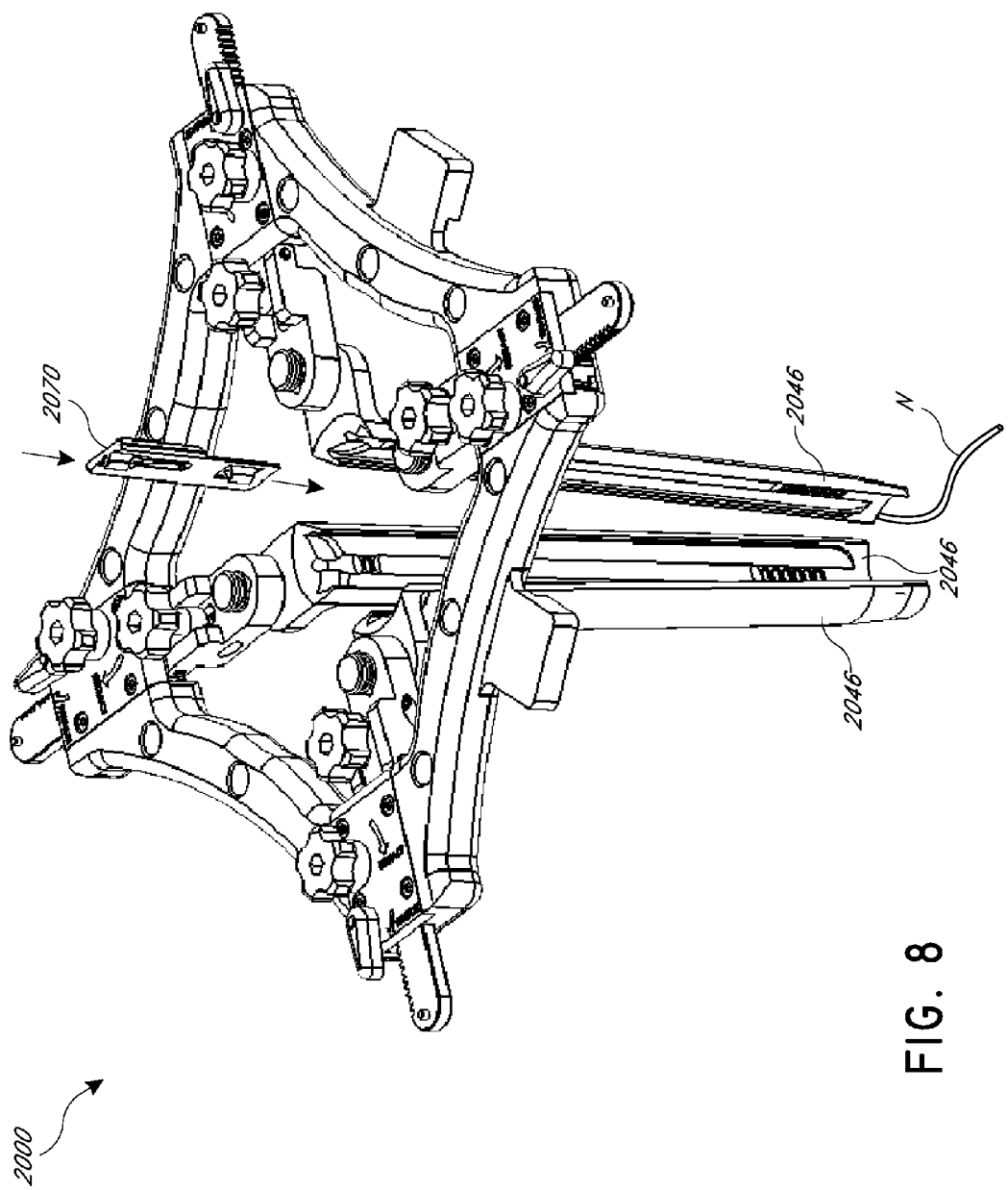

In certain instances, it is desirable or necessary to effectively extend the length of one or more blades 2040 of the retractor. For example, as illustrated in FIG. 8, the distal end of a blade 2040 may not be long enough to reach the depth of a nerve bundle N or other portion of the anatomy that must be carefully retracted or moved by the blade 2040. Thus, in some embodiments, as illustrated in FIGS. 8-13, one or more of the blades 2040 can be configured to receive a shim or other extension portion 2070.

Figures 15A, 15B:
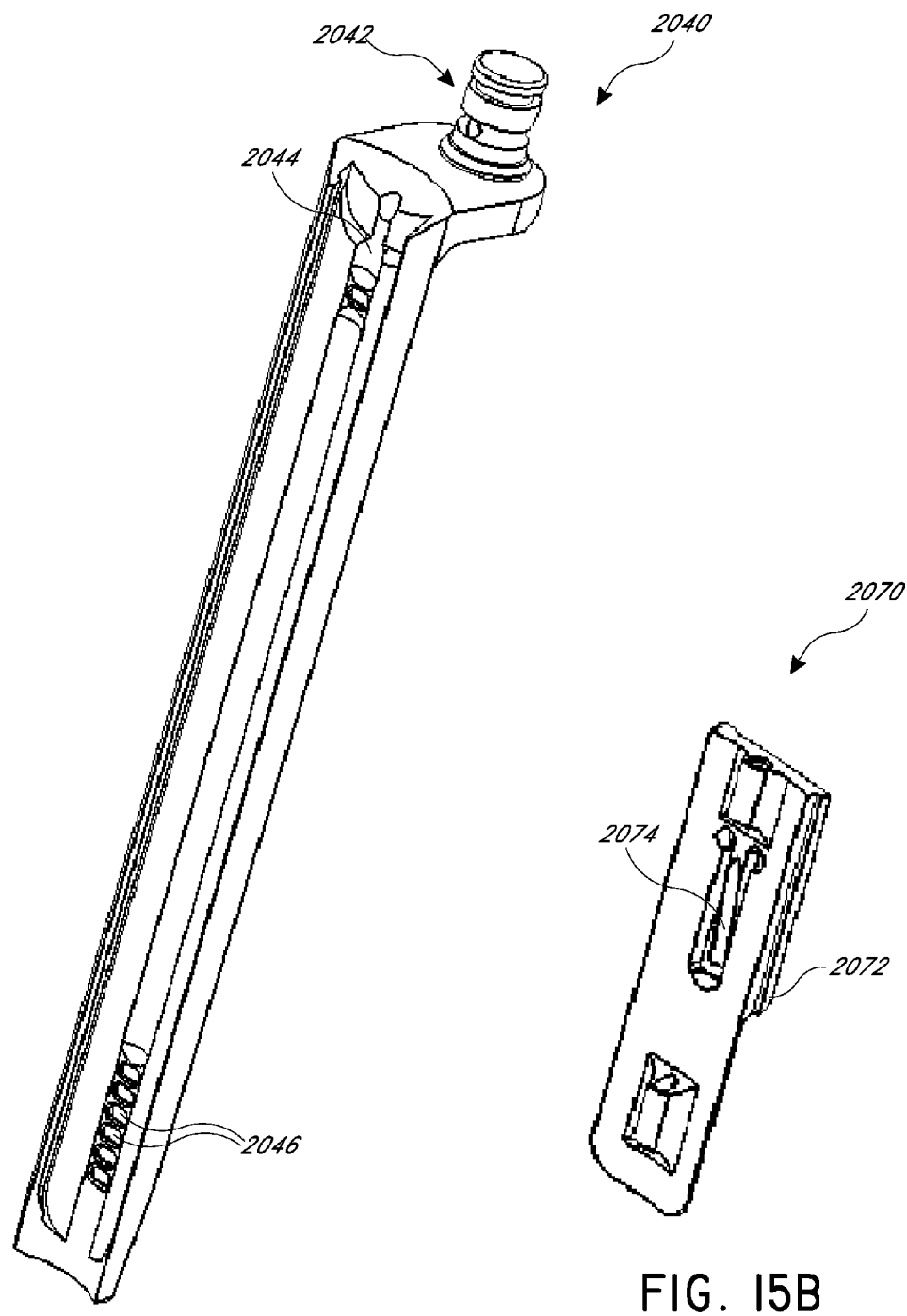
FIG. 15A illustrates a perspective view of a blade configured to secure to a retractor according to one embodiment.
FIG. 15B illustrates a perspective view of a shim configured to be received within a channel or other portion of a blade according to one embodiment.
Figure 16:
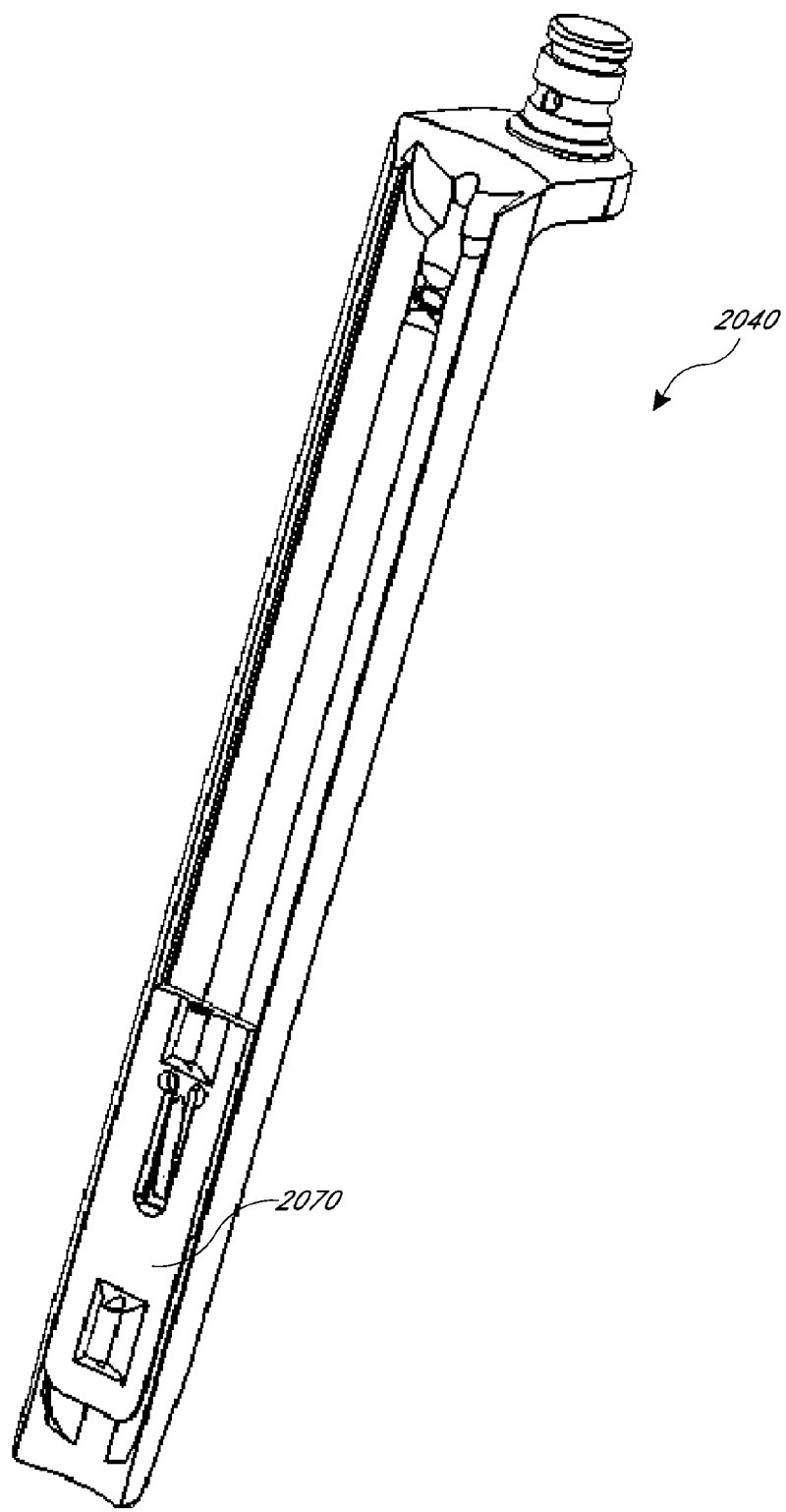
FIG. 16 illustrates the shim of FIG. 15B cooperatively secured to the blade of FIG. 15A.

With reference to FIGS. 15A, 15B and 16, the lengthening shim or extender portion 2070 can be configured to slide within a corresponding channel, slot or other opening 2044 of the blade 2040. For instance, in one embodiment, the lengthening shim 2070 comprises a flange or other protruding portion or feature 2072 that is sized, shaped and otherwise configured to be received by the slot or channel 2044 of the blade 2040. In some embodiments, therefore, such a shim 2070 can be coupled to a blade 2040 and be advanced along the distal end of the blade 2040. In some embodiments, if the shim 2070 is moved far enough into the blade's channel 2044, the shim will engage the blade 2040 in such a manner so that it cannot be easily withdrawn (e.g., proximally relative to the blade). For example, the shim and the corresponding distal portion of the blade can comprise a ratchet and/or other positive engagement feature or mechanism. This can help ensure that the shim 2070 will perform as needed (e.g., to act as an extension along the distal end of blade 2040). In some embodiments, a special release or other feature can be included to permit the user to retract the shim or other extender against a ratchet or other positive engagement feature or mechanism. As mentioned above and discussed in greater detail below with reference to FIGS. 18 and 19, one or more light or other illumination devices or components (e.g., a removable fiber optic light attachment) can be sized, shaped and/or otherwise configured to be positioned into and moved within a slot, channel or other opening of a blade. Thus, the targeted area of the patient or other subject can be advantageously illuminated to assist the surgeon or other practitioner to execute a particular procedure.

One embodiment of how the shim or other extending portion 2070 can be used to enhance the tissue retraction capabilities of the retractor is illustrated in the time-sequential images of FIGS. 8-13. As shown, once a surgeon or other practitioner appreciates that the length of one or more blades needs to be extended, he or she can connect a shim or other extension device or component to the corresponding blade members. In some embodiments, as illustrated and discussed herein, such shims or extenders are sized, shaped and/or otherwise configured to fit within and be moved relative to a slot, channel or other feature of the blade. However, in other embodiments, such extenders can attach to the blades using one or more other devices or methods, as desired or required.

According to some embodiments, for example, the shims or other extender portions can be pushed, urged or other moved toward the distal ends of the corresponding blades 2040 (e.g., until there is a positive engagement with a ratchet mechanism) using any elongated tool or member.

Figure 9:
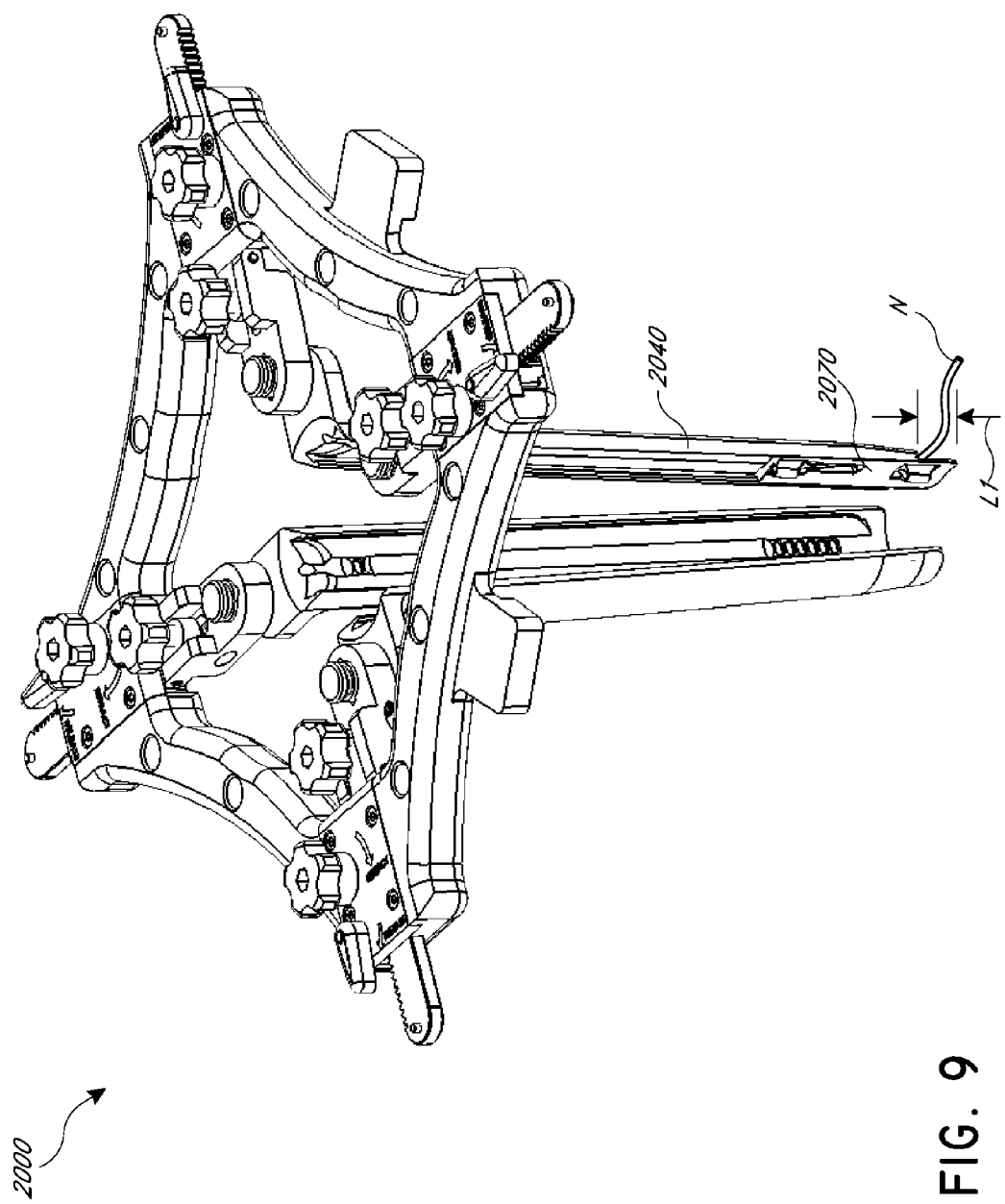
Figure 10:
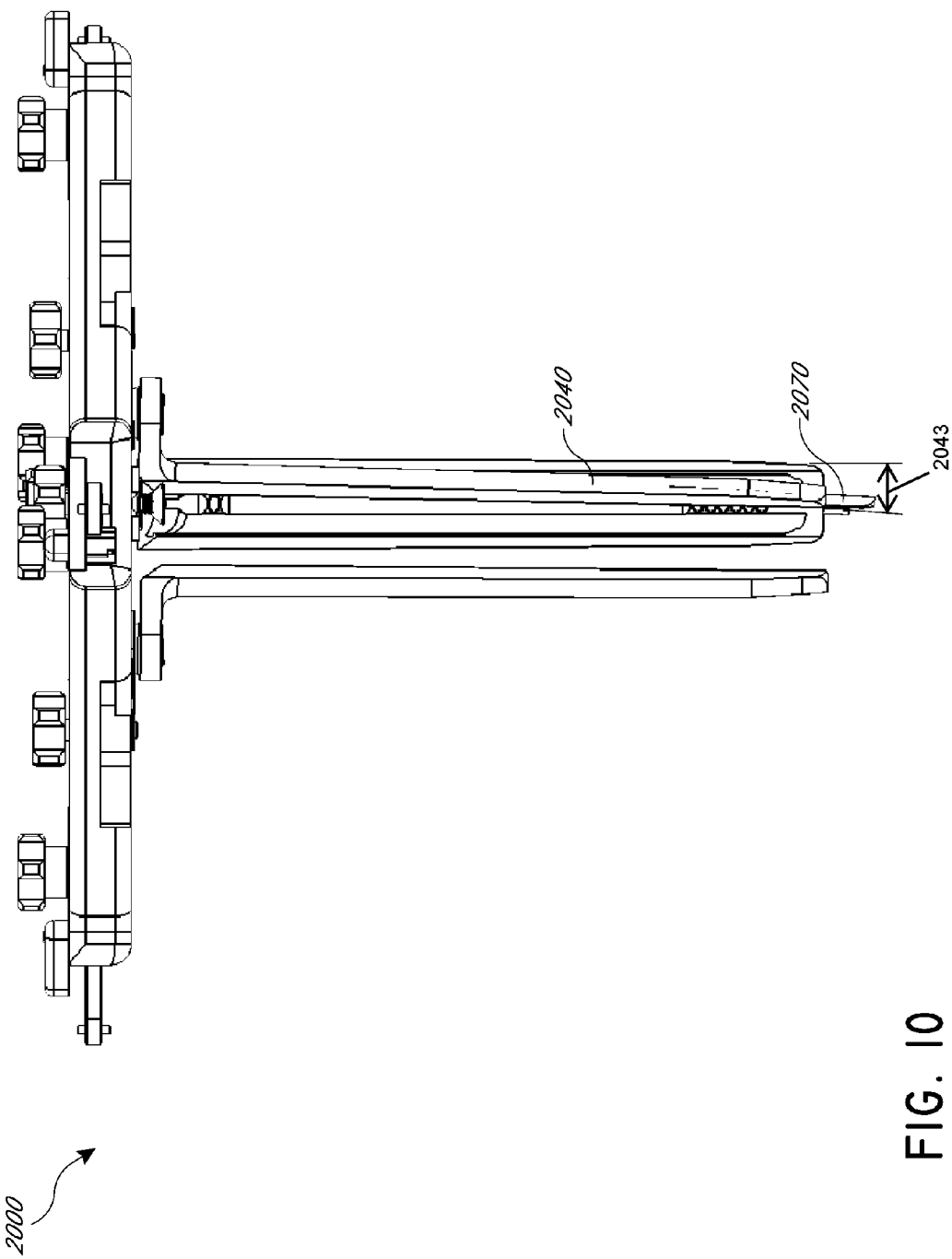
Figure 11:
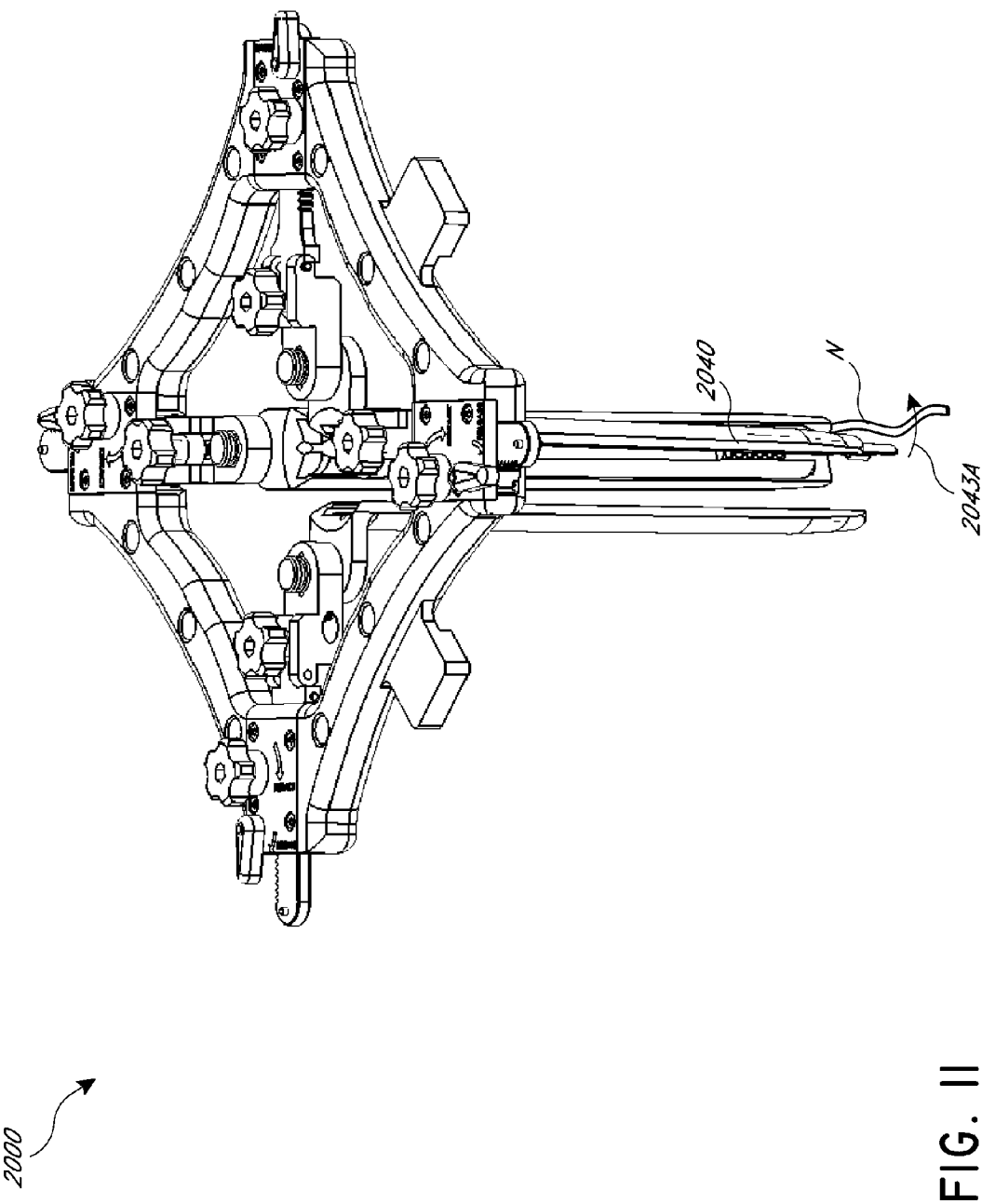
Figure 12:
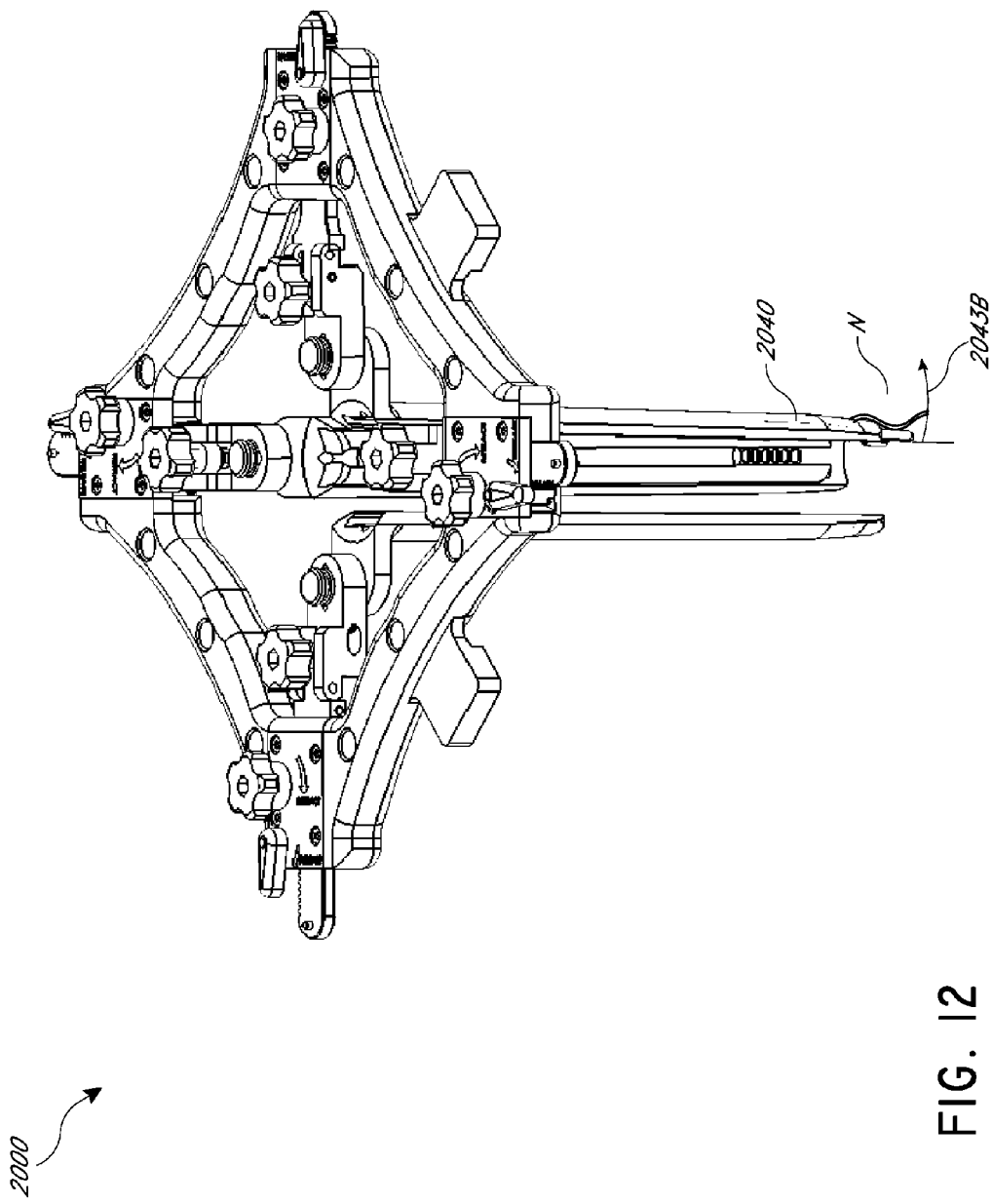
Figure 13:
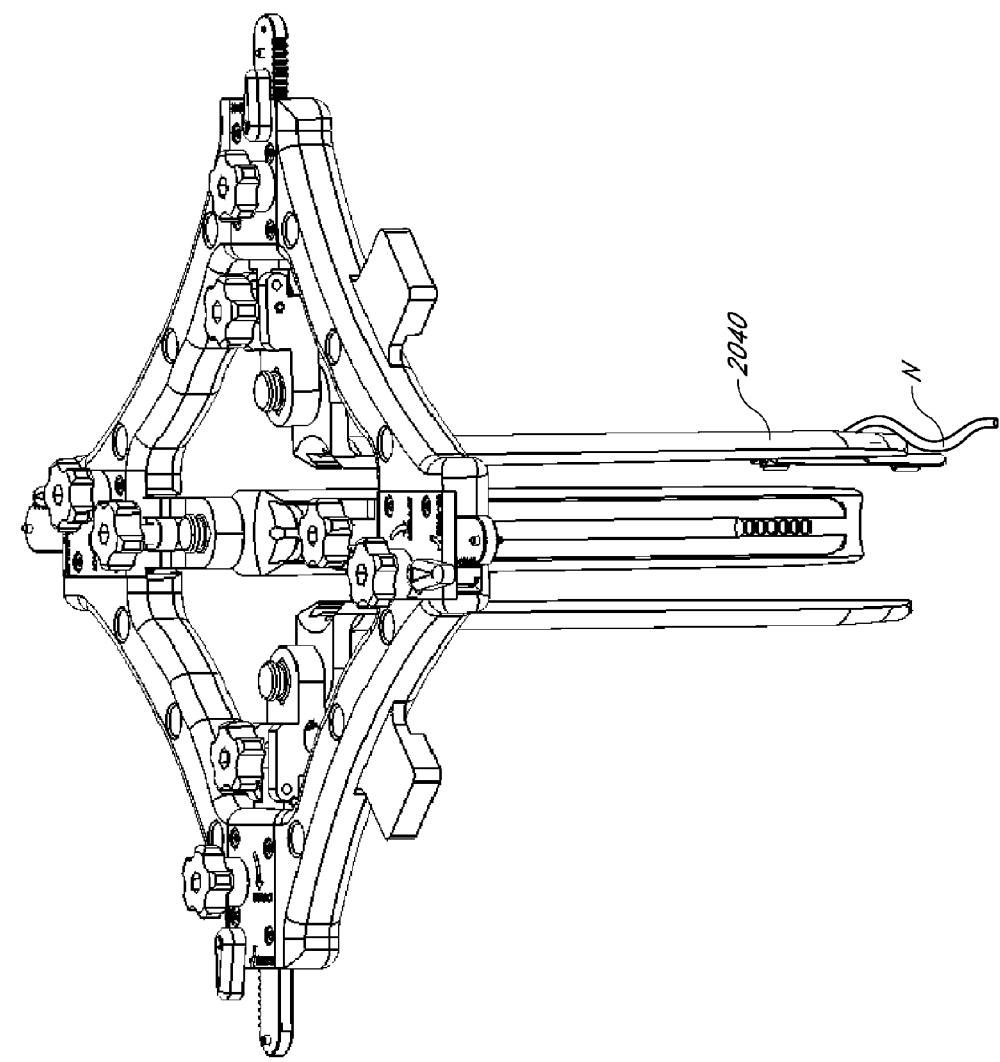

With continued reference to FIGS. 9 and 10, the angle and/or lateral position of the corresponding blade 2040 may need to be adjusted in order to get around a particular portion of the anatomy (e.g., a nerve or nerve bundle, organ, muscle tissue and/or other sensitive area of the anatomy that needs to be moved by the blade). Thus, as noted above, one or more blades can be dragged and/or swept as needed. In some embodiments, the retractor disclosed herein is configured so that one or more of the blades 2040 can be selectively swept (e.g., in a direction generally represented by arrow 2043 in FIG. 10) past the center-point CP of the retractor. This helps increase the flexibility of the retractor and allows the surgeon to carefully retract or move tissue to levels that otherwise may not have been possible.

Thus, a surgeon can selectively manipulate one more dials to precisely and easily move one or more of the blades into any one of a number of positions during a retraction procedure. For example, with the assistance of a lengthening shim or extender portion 2070 secured to one of the blades 2040, the practitioner can carefully move a nerve bundle N, muscle tissue and/or other desired anatomical area along the outside of the blade 2040 (see, e.g., FIGS. 8-13). In some embodiments, the length of the lengthening shim 2070 is approximately one inch. However, the length of the shim 2070 can be greater than 1 inch (e.g., 1.5, 2 inches, more than 2 inches, values between the foregoing lengths, etc.) or shorter than 1 inch (e.g., 0.1, 0.2, 0.3, 0.4, 0.5, 0.6, 0.7, 0.8, 0.9, 0.95 inches, less than about 0.1 inches, values between the foregoing lengths, etc.), as desired or required.

To assist in the description of the disclosed embodiments, words such as upward, upper, bottom, downward, lower, rear, front, vertical, horizontal, upstream, downstream have been used above to describe different embodiments and/or the accompanying figures. It will be appreciated, however, that the different embodiments, whether illustrated or not, can be located and oriented in a variety of desired positions.

As discussed herein, one or more of the blades can be configured to advantageously move past the center-point CP of the retractor device (e.g., the center-point of the retractor's main opening if all blades have the same or similar lateral orientation). Thus, the blades can be used to easily and quickly access a particular portion of the spine (or other portion of the subject's anatomy) while selectively and safely moving sensitive tissues (e.g., nerves, organs, etc.) around the opening (e.g., to create a desired clearance or accessway).

Figure 14:
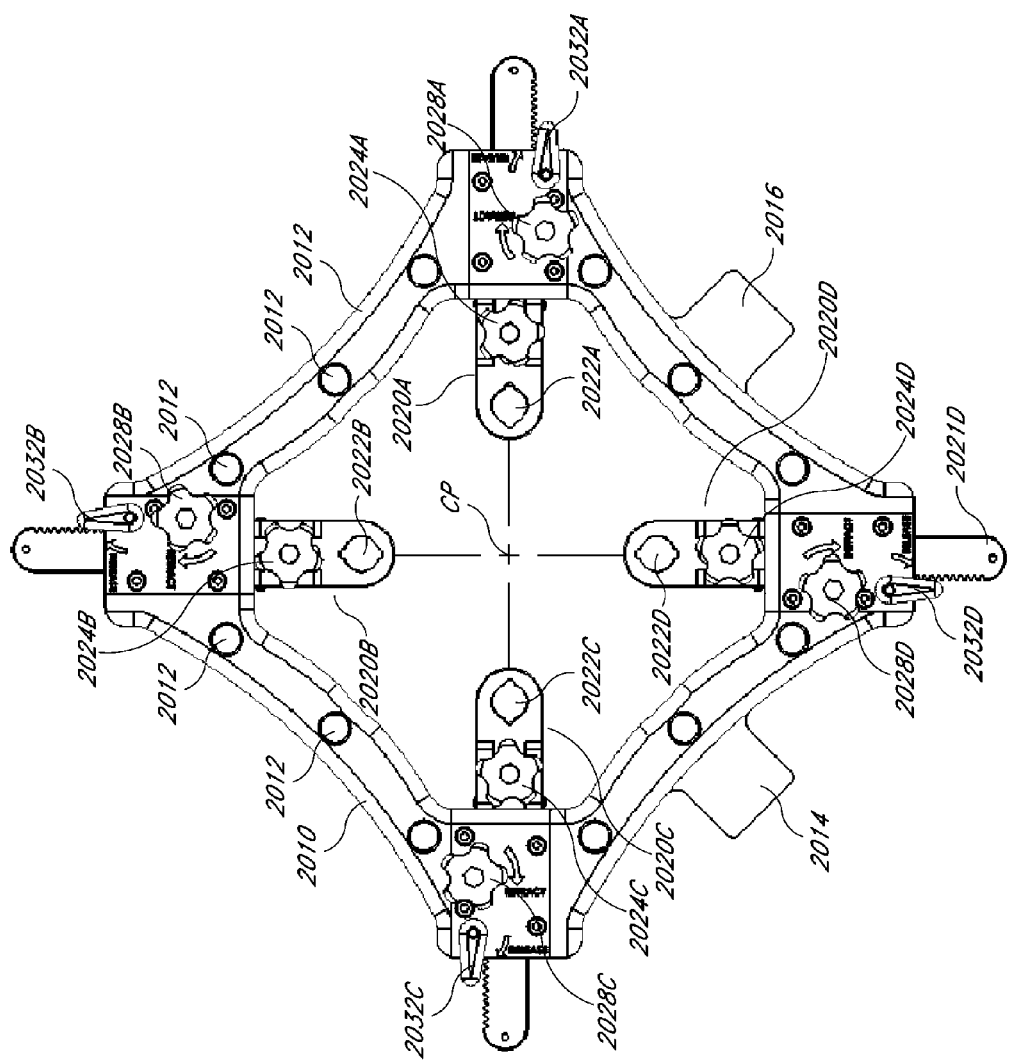
FIG. 14 illustrates a top view of the retractor of FIGS. 1-13.

With continued reference to FIGS. 14, 15A and 15B, the blades 2040 can be removably secured within corresponding recesses 2022A-D of the movable members of the retractor. Accordingly, the blades can be easily removed and/or replaced, as desired or required (e.g., for maintenance, sterilization, etc.).

Figure 17:
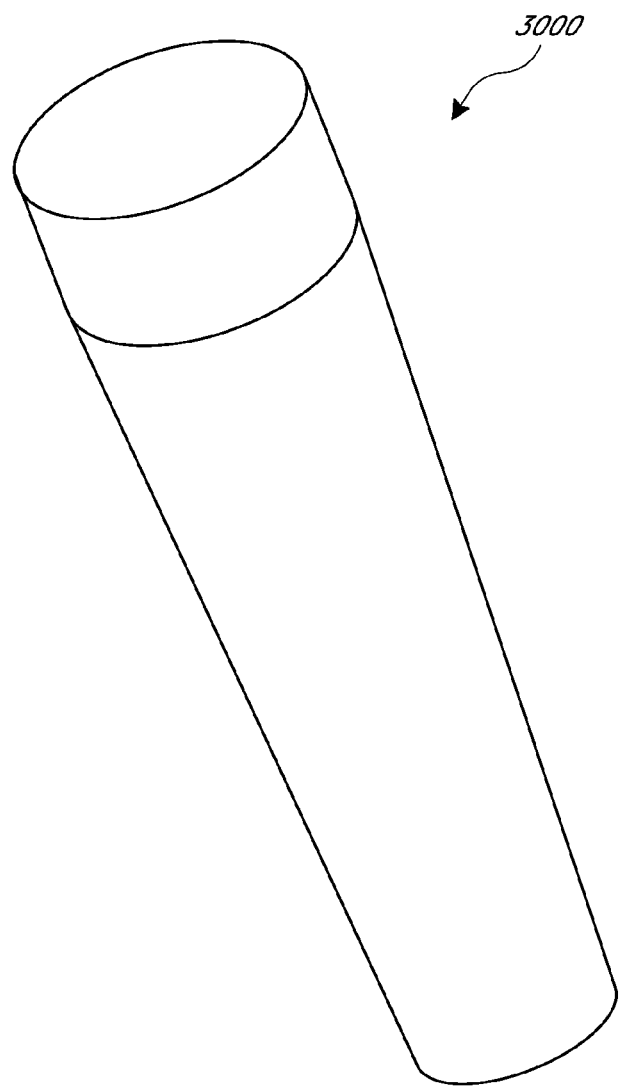
FIG. 17 illustrates a perspective view of an alignment device configured to be used with the retractor.

According to some embodiments, a generally solid alignment device can be used to generally align and orient the different blades of a retractor relative to one another. FIG. 17, for example, illustrates one embodiment of such an alignment device 3000. In some arrangements, the alignment device 3000 comprises a generally closed outer surface. In some embodiments, the outer diameter of the alignment device 3000 (which can be referred to as a drone dilator or dilator guide) matches or substantially matches the outer diameter of a dilator or similar device that has been inserted into the subject prior to using the retractor. For example, in some embodiments, the outer diameter of the alignment device 3000 is approximately 18 mm. However, in other embodiments, the outer diameter of the device 3000 can be smaller than 18 mm (e.g., about 16 mm, 14 mm, 12 mm, 10 mm, less than about 10 mm) or greater than 18 mm (e.g., about 20 mm, 22 mm, greater than about 22 mm), as desired or required.

In some embodiments, once the largest dilator has been inserted into the patient or other subject, the surgeon or other clinician can use a retractor 2000 similar to any of the embodiments disclosed herein. The blades of the retractor can be moved (e.g., using knobs, release levers and/or other controllers) so as to snugly or substantially snugly surround the exterior of the alignment device 3000, as illustrated in FIG. 18. In some embodiments, the blades can be adjusted so their interior surfaces substantially contact the exterior surface of the alignment device 3000. As shown, the surgeon can hold the blades of the retractor 2000 in place around the alignment device 3000 and align the alignment device over the largest dilator positioned within the subject. With the device 3000 aligned with the dilator, the surgeon can advance the retractor 2000 into the patient, such that the blades move along the outside surface of the largest dilator. This provides a convenient, consistent and reliable method of inserting the retractor blades into the subject. As the blades move downwardly into the subject's anatomy, the alignment device 3000 will stay in place, effectively allowing the device 3000 to be moved relative to the blades and the rest of the retractor. As discussed herein, once the retractor blades have been properly advanced into the subject, the alignment device 3000 and/or any dilators can be removed from the subject.

According to some embodiments, the alignment device 3000 comprises one or more plastic and/or other materials. For example, the device 3000 can comprise polyoxymethylene (POM), also known as acetal, polyacetal or polyformaldehyde. However, any other plastic, composite, metal, alloy and/or other material can be included in the device 3000, as desired or required. The device 3000 is advantageously configured to withstand the forces, moments and/or other elements to which it may be exposed, both during a procedure and during related tasks (e.g., cleaning or sterilization, transport, etc.).

With further reference to FIG. 18, a light or illumination device or component 4000 can be sized, shaped and/or otherwise configured to secure to one or more blades and/or another portion of the retractor 2000. A detailed view of the embodiment of the illumination device 4000 of FIG. 18 is illustrated in FIG. 19. As shown, the illumination device 4000 can comprise a hub or other coupling 4040 (e.g., for attachment to a light source), a flexible cable 4020 and the illumination output portion 4010. In some embodiments, the illumination output portion 4010 is sized, shaped and/or otherwise configured to be releasably inserted (e.g., at least partially) within a slot, channel or other receiving feature or portion of a blade, as illustrated in FIG. 18. Thus, one or more illumination devices 4000 can be secured to a retractor device 2000 to provide light to the anatomical area of the subject being accessed. According to some embodiments, the light device 4000 comprises fiber optic technology, LED and/or any other source to generate light.

Although the subject matter provided in this application has been disclosed in the context of certain specific embodiments and examples, it will be understood by those skilled in the art that the inventions disclosed in this application extend beyond the specifically disclosed embodiments to other alternative embodiments and/or uses of the subject matter disclosed herein and obvious modifications and equivalents thereof. In addition, while a number of variations of the inventions have been shown and described in detail, other modifications, which are within the scope of these inventions, will be readily apparent to those of skill in the art based upon this disclosure. It is also contemplated that various combinations or subcombinations of the specific features and aspects of the embodiments may be made and still fall within the scope of the inventions disclosed herein. Accordingly, it should be understood that various features and aspects of the disclosed embodiments can be combine with or substituted for one another in order to form varying modes of the disclosed inventions. Thus, it is intended that the scope of the subject matter provided in the present application should not be limited by the particular disclosed embodiments described above, but should be determined only by a fair reading of the claims that follow.

What is claimed is:

1. A retractor device for selectively moving anatomical tissue of a subject during a minimally invasive procedure, comprising:
   a main body comprising a generally rectangular shape, said main body defining a central opening, said central opening comprising a center-point positioned along a centerline of said central opening;
   a plurality of movable members secured to the main body;
   a blade secured to each movable member and configured to be moved together with a corresponding movable member to which said blade is secured;
   wherein each blade extends generally perpendicular to the main body, said blade comprising a distal end configured to extend into an anatomy of the subject;
   wherein each movable member is configured to move laterally relative to the main body, such that the blades secured to the movable members can be moved within the central opening defined by the main body;
   wherein each of the blades is configured to be selectively moved laterally past the center-point of the central opening;
   wherein each of the blades is configured to be selectively independently rotated relative to: (i) an axis generally perpendicular to the main body, and (ii) each of the other blades;
   wherein the movable members are configured to be moved relative to one another so that the blades attached to said movable members generally form a cylindrical opening within the central opening defined by the main body; and
   wherein each movable member is operatively coupled to a first controller and a second controller, said first controller being configured to selectively adjust a lateral position of the movable member, and said second controller being configured to selectively rotate the blade attached to said movable member.

2. The retractor device of claim 1, wherein each of the blades is removably secured to a corresponding movable member.

3. The retractor device of claim 1, wherein at least one of the first controller and the second controller comprises a rotatable knob.

4. The retractor device of claim 1, wherein the movable members are moved using a rack and pinion mechanism.

5. The retractor device of claim 1, wherein the blade comprises at least one slot.

6. The retractor device of claim 5, wherein the at least one slot of the blade is configured to slidably receive a shim, said shim being configured to generally extend a distal end of said blade.

7. The retractor device of claim 5, wherein the at least one slot of the blade is configured to slidably receive an illumination device, said illumination device being configured to provide light to a portion of the subject's anatomy being accessed.

8. The retractor device of claim 7, wherein the illumination device comprises a fiber-optic or LED light source.

9. The retractor device of claim 1, wherein the main body forms a diamond or square shape.

10. A retractor device for selectively moving anatomical tissue of a subject during a minimally invasive procedure, comprising:
    a main body comprising at least three sides, said main body defining a central opening, said central opening comprising a center-point positioned along a centerline of said central opening;
    a plurality of movable members secured to the main body;
    a blade secured to each movable member and configured to be moved together with a corresponding movable member to which said blade is secured;
    wherein each blade extends generally perpendicular to the main body, said blade comprising a distal end configured to extend into an anatomy of the subject;
    wherein each movable member is configured to move laterally relative to the main body, such that the blades secured to the movable members can be moved within the central opening defined by the main body;
    wherein each of the blades is configured to be selectively moved laterally past the center-point of the central opening;
    wherein each of the blades is configured to be selectively independently rotated relative to: (i) an axis generally perpendicular to the main body, and (ii) each of the other blades;
    wherein the movable members are configured to be moved relative to one another so that the blades attached to said movable members generally form a cylindrical opening within the central opening defined by the main body; and
    wherein each movable member is operatively coupled to a first controller and a second controller, said first controller being configured to selectively adjust a lateral position of the movable member, and said second controller being configured to selectively rotate the blade attached to said movable member.

11. The retractor device of claim 10, wherein the main body comprises four or more sides.

12. The retractor device of claim 10, wherein each of the blades is removably secured to a corresponding movable member.

13. The retractor device of claim 10, wherein at least one of the first controller and the second controller comprises a rotatable knob.

14. The retractor device of claim 10, wherein the movable members are moved using a rack and pinion mechanism.

15. The retractor device of claim 10, wherein the blade comprises at least one slot.

16. The retractor device of claim 15, wherein the at least one slot of the blade is configured to slidably receive a shim, said shim being configured to generally extend a distal end of said blade.

17. The retractor device of claim 15, wherein the at least one slot of the blade is configured to slidably receive an illumination device, said illumination device being configured to provide light to a portion of the subject's anatomy being accessed.

18. The retractor device of claim 17, wherein the illumination device comprises a fiber-optic or LED light source.

* * * * *